(12) United States Patent  
Djakov et al.

(10) Patent No.: US 8,297,110 B2  
(45) Date of Patent: Oct. 30, 2012

(54) FLUID PROBE

(75) Inventors: Vladislav Djakov, Warrington (GB); Ejaz Huq, Warrington (GB); Richard John Dunn, Reading (GB)

(73) Assignee: Microvisk Limited, St Asaph, Denbighshire (GB)

( * ) Notice: Subject to any disclaimer, the term of this patent is extended or adjusted under 35 U.S.C. 154(b) by 882 days.

(21) Appl. No.: 12/293,234

(22) PCT Filed: Mar. 14, 2007

(86) PCT No.: PCT/GB2007/000887  
§ 371 (c)(1),  
(2), (4) Date: Sep. 16, 2008

(87) PCT Pub. No.: WO2007/104978  
PCT Pub. Date: Sep. 20, 2007

(65) Prior Publication Data  
US 2009/0084167 A1   Apr. 2, 2009

(30) Foreign Application Priority Data  
Mar. 16, 2006  (GB) .................................. 0605273.2

(51) Int. Cl.  
*G01N 11/10* (2006.01)

(52) U.S. Cl. ..................................................... 73/54.24

(58) Field of Classification Search ...... 73/54.24–54.34, 73/54.38  
See application file for complete search history.

(56) References Cited

U.S. PATENT DOCUMENTS

| | | | |
|---|---|---|---|
| 3,282,084 A | 11/1966 | Banks | |
| 4,695,956 A | 9/1987 | LeVeen et al. | |
| 5,771,902 A | 6/1998 | Lee et al. | |
| 5,780,727 A | 7/1998 | Gimzewski et al. | |
| 6,044,694 A | 4/2000 | Anderson et al. | |
| 6,182,499 B1 | 2/2001 | McFarland et al. | |
| 6,249,001 B1 | 6/2001 | Sauer et al. | |

(Continued)

FOREIGN PATENT DOCUMENTS

DE          10029091          1/2002

(Continued)

OTHER PUBLICATIONS

Thaysen, J. et al., "SU-8 Based Piezoresistive Mechanical Sensor," The Fifteenth IEEE International Conference on Micro Electro Mechanical Systems, 2002, Las Vegas, pp. 320-323.

(Continued)

*Primary Examiner* — John Fitzgerald  
(74) *Attorney, Agent, or Firm* — Bingham Greenebaum Doll LLP

(57) ABSTRACT

A device for measuring the properties of a fluid, a method of manufacture, and a method of operation is described. The device includes a body region, a first flexible element and a second flexible element. Each flexible element has a first end and a second end, the first end being fixedly located on the body region. Each flexible element is moveable from at least a first respective configuration to a second respective configuration via bending of the element. The first flexible element includes an actuating portion arranged to move the flexible element between the first configuration and the second configuration. The second flexible element includes an integral movement sensor for sensing movement of the flexible element. The first flexible element is coupled to the second flexible element at a position distant from the body region. Only the actuating portion of the first flexible element is operable to move the first and second flexible elements.

29 Claims, 12 Drawing Sheets

U.S. PATENT DOCUMENTS

| | | | |
|---|---|---|---|
| 6,260,408 B1 | 7/2001 | Vig et al. | |
| 6,269,685 B1 | 8/2001 | Oden | |
| 6,269,686 B1 | 8/2001 | Hahn | |
| 6,311,549 B1 | 11/2001 | Thundat et al. | |
| 6,436,647 B1 | 8/2002 | Quate et al. | |
| 6,457,360 B1 | 10/2002 | Daraktchiev et al. | |
| 6,575,020 B1 | 6/2003 | de Charmoy Grey et al. | |
| 6,679,055 B1 | 1/2004 | Ellis | |
| 7,047,794 B2 | 5/2006 | Hajduk et al. | |
| 7,257,984 B2* | 8/2007 | Pidria et al. | 73/10 |
| 7,775,084 B2* | 8/2010 | Huq et al. | 73/54.27 |
| 2003/0056574 A1 | 3/2003 | Drahm et al. | |
| 2003/0062193 A1 | 4/2003 | Thaysen et al. | |
| 2007/0033990 A1 | 2/2007 | Grey et al. | |
| 2007/0272002 A1 | 11/2007 | Jakoby | |
| 2008/0011058 A1 | 1/2008 | Lal et al. | |
| 2008/0028837 A1* | 2/2008 | Djakov et al. | 73/54.38 |
| 2010/0251806 A1* | 10/2010 | Djakov et al. | 73/54.38 |

FOREIGN PATENT DOCUMENTS

| | | |
|---|---|---|
| EP | 1674865 | 6/2006 |
| GB | 2359368 | 8/2001 |
| GB | 2369887 | 6/2002 |
| JP | 2001150393 | 6/2001 |
| WO | 9947908 | 9/1999 |
| WO | 0039537 | 7/2000 |
| WO | 0066266 | 11/2000 |
| WO | 0212443 | 2/2002 |
| WO | 03022731 | 3/2003 |
| WO | 03062135 | 7/2003 |
| WO | 03067248 | 8/2003 |
| WO | 03071258 | 8/2003 |
| WO | 03104784 | 12/2003 |
| WO | 2004059306 | 7/2004 |
| WO | 2004083802 | 9/2004 |
| WO | 2005054817 | 6/2005 |
| WO | 2007104978 | 9/2007 |
| WO | 2009022121 | 2/2009 |

OTHER PUBLICATIONS

Djakov, V. et al., "Bimorph Actuators for MOEMS," Proc. SPIE vol. 4755, pp. 804-814, Design, Test, Integration, and Packaging of MEMS/MOEMS 2002.

Coutinho, M.G. et al., "The Intelligent Motion Surface: A hardware/software tool for the assembly of meso-scale devices," IEEE International Conference on Robotics, and Automation, Albuquerque, NM, 1997.

Suh, J.W. et al., "Organic thermal and electrostatic ciliary microactuator array for object manipulation," Sensors and Actuators A58 (1997), pp. 51-60.

Riethmuller, W. et al., "Thermally Excited Silicon Microactuators," IEEE Transactions on Electron Devices, vol. 35: No. 6, Jun. 1988.

Ataka, M. et al., "Fabrication and Operation of Polymide Bimorph Actuators for a Ciliary Motion System," Journal of Microelectromechanical Systems, vol. 2: No. 4, Dec. 1993, pp. 146-150.

Que et al., "Bent-Beam Electrothermal Actuators—Part I: Single Beam and Cascaded Devices," Journal of Microelectromechanical Systems, vol. 10, No. 2, pp. 247-254, Jun. 2001.

PCT/JP2005/008755, International Preliminary Report on Patentability, dated Nov. 14, 2006.

* cited by examiner

06_01_064.bmp Chip 2 in Air

08_01_061.bmp Chip 2 in Water

08_01_064.bmp Chip 2 in 10cPs Silicone Oil

FLUID PROBE

FIELD

The present invention relates to a probe for the determination of properties of fluids, and to methods of manufacture and use of such probes. The probe is suitable for, although not restricted to, the determination of the relative change in viscosity of fluids such as blood.

SUMMARY

Sensors are known that use microscopic flexible mechanical structures such as micro-cantilevers. Micro-cantilevers are devices in which changes in the mechanical properties of the microscopic micro-cantilever can be used to detect changes in the environment of the micro-cantilever. Micro-cantilevers are made of a material such as silicon, silicon nitride, glass, or metal, typically using micromachining techniques. For example, U.S. Pat. No. 6,575,020 describes various micro-cantilevers integrated in micro-liquid handling systems, and how such micro-liquid handling systems can be utilised to monitor the physical, chemical and biological properties of the fluids in such systems. Various configurations of the device are described, including a triangular micro-cantilever configuration, in which a piezoresistor is placed upon each of the two arms, enabling torsion as well as vertical deflection of the micro-cantilever to be detected.

One disadvantage of typical micro-cantilever arrangements is that the cantilever is formed of a relatively rigid material, thus limiting the deflection range (and hence potential sensitivity) of the sensor.

International Patent Application No. PCT/GB2004/005079, published as WO 2005/054817, describes a number of different implementations of a device for detecting a property of a fluid, by using a flexible element. The flexible element can be formed of two layers having different coefficients of thermal expansion. A heater can be incorporated into the flexible element, such that the element moves from a first configuration to a second configuration. When the heat is removed, the element can then relax back to the first configuration. An appropriate piezoresistive material can be used to determine the degree or rate of deflection of the element. Such a flexible element allows a relatively accurate measurement to be made of the viscosity change over time due to the relatively large amount of deflection that can be achieved by the element.

It is an aim of embodiments of the present invention to address one or more problems of the prior art, whether referred to herein or otherwise. It is an aim of particular embodiments of the present invention to provide a fluid probe of enhanced sensitivity.

In a first aspect, the present invention provides a device for detecting a property of a fluid, comprising: a body region; a first flexible element and a second flexible element, each flexible element having a first end and a second end, said first end being fixedly located on said body region, and each flexible element being moveable from at least a first respective configuration to a second respective configuration via bending of the element; said first flexible element comprising an actuating portion arranged to move the flexible element between the first configuration and the second configuration; said second flexible element comprising an integral movement sensor for sensing movement of the flexible element, and wherein said first flexible element is coupled to said second flexible element at a position distant from said body region, and only the actuating portion of said first flexible element is operable to move the first and second flexible elements.

As the first and second flexible elements are coupled to each other, movement of the first flexible element(s) results in the movement of both first and second flexible elements. This allows the sensor(s) within the second flexible element to more accurately determine the movement of the second flexible element(s), allowing increased accuracy and/or sensitivity in determining the properties of the fluid in which the flexible elements are moved. This increased sensitivity arises due to a decrease in the noise affecting the sensor(s) arising from the actuator portion(s), as the relevant actuator portion(s) and sensor portion(s) are located in different flexible elements. This noise can take the form of thermal noise or electrical noise.

Each of said flexible elements may extend longitudinally, substantially parallel to each other.

Each flexible element may move from said first configuration to said second configuration via bending of the element in a respective bending plane, and the elements may be coupled together via a coupling member extending between the first and second elements in a direction substantially perpendicular to the bending planes.

Said coupling member may be formed of a substantially rigid material.

Said coupling member may be connected to the second ends of the first and second flexible elements.

Said coupling member may extend in a plane away from the first and second flexible elements.

The coupling member may be shaped to act as a paddle as the flexible members move between said first and second configurations.

The device may comprise at least two of said first flexible elements, the second flexible element being located between the two first flexible elements.

Said first flexible element may be coupled to said second flexible element via a thermally insulative material.

Said first flexible element may be coupled to said second flexible element at a plurality of positions.

Said first and second flexible elements may extend longitudinally, with the first flexible element being coupled to said second flexible element along the complete length of said elements.

The actuating portion of said first flexible element may comprise a laminate of at least two layers, having different coefficients of thermal expansion; a heater element for heating the flexible element to induce bending of the element.

A first layer of the laminate may comprise a polymer, and a second layer of the laminate may comprise a metal.

A first layer of the laminate may comprise a polymer, and a second layer of the laminate may comprise a polymer.

Said layers may have a Young's modulus of less than 100 GPa, and a coefficient of thermal expansion at room temperature of greater than $10^{-6}$/K.

Said movement sensor may be arranged such that an electrical property of the movement sensor changes due to movement of said second flexible element.

Said movement sensor may comprise a piezoresistive element arranged such that the electrical resistance of the piezoresistive element changes as the second flexible element bends.

Said piezoresistive element may comprise at least one of nichrome, chromium, copper, and chrome copper alloy.

Said piezoresistive element may comprise at least one of AlN (Aluminium Nitride), PZT, polycrystalline silicon, electrically conductive polymers.

The length of the flexible elements from the first end to the second end may be within the range 100 to 1000 μm.

The distance between the second end of the second flexible element in said first configuration and the second end of the second flexible element in said second configuration may lie within the range 20 to 650 μm.

The device may further comprise an electronic circuit coupled to the first flexible element and arranged to provide a signal to the actuator portion for moving a first flexible element from the first configuration to the second configuration, and coupled to the movement sensor of the second flexible element, and arranged to provide an output signal indicative of the movement sensed by said movement sensor.

In a second aspect, the present invention provides a method of manufacturing a device for detecting a property of a fluid, comprising: providing a body region; providing a first flexible element and a second flexible element, each flexible element having a first end and a second end, said first end being fixedly located on said body region, each flexible element being movable from at least a first respective configuration to a second respective configuration by bending of said element, the first flexible element comprising an actuating portion arranged to move the flexible element between the first and second configurations, and the second flexible element comprising an integral movement sensor for sensing movement of the flexible element; forming the first flexible element and the second element with a coupling extending between the flexible elements at a position distant from said body region; and configuring only the actuation portion of the first flexible element to be operable to move the first and second flexible elements.

The method may further comprise the step of providing a layer of metal arranged to act as an etch-stop layer during patterning of the flexible elements, and to allow subsequent release of the flexible elements from the surrounding structure.

The metal may be chromium. The metal may be titanium.

The method may further comprise the step of forming each flexible element comprising at least one conductive material, and forming the coupling from non-conductive material.

In a third aspect, the present invention provides a method of determining a property of a fluid using first and second flexible elements fixedly located at one end on a body region, and coupled together at a position distant from the body region, the method comprising: actuating the first flexible element to bend from a first configuration to a second configuration, the second flexible element being moved from a respective first configuration to a second respective configuration due to being coupled to the first flexible element; sensing movement of the second flexible element; and determining at least one property of the fluid by processing of the sensed movement.

The method may comprise actuating said first flexible element to move between the first and second configurations at a frequency of less than 10 Hz.

Said first flexible element may be actuated to move from the first configuration to the second configuration such that an end of the first flexible element is displaced by at least 100 μm.

In a fourth aspect, the present invention provides a device for detecting a property of a fluid, substantially as described herein within reference to the accompanying Figures.

In a fifth aspect, the present invention provides a method of measuring a property of a fluid using at least two flexible elements, substantially as described herein with reference to the accompanying Figures.

In a sixth aspect, the present invention provides a method of manufacturing a device, substantially as described herein, with reference to the accompanying Figures.

Preferred embodiments of the present invention will now be described, by way of example only, with reference to the accompanying figures, in which:

DETAILED DESCRIPTION OF THE ILLUSTRATED EMBODIMENTS

Figure 1A:
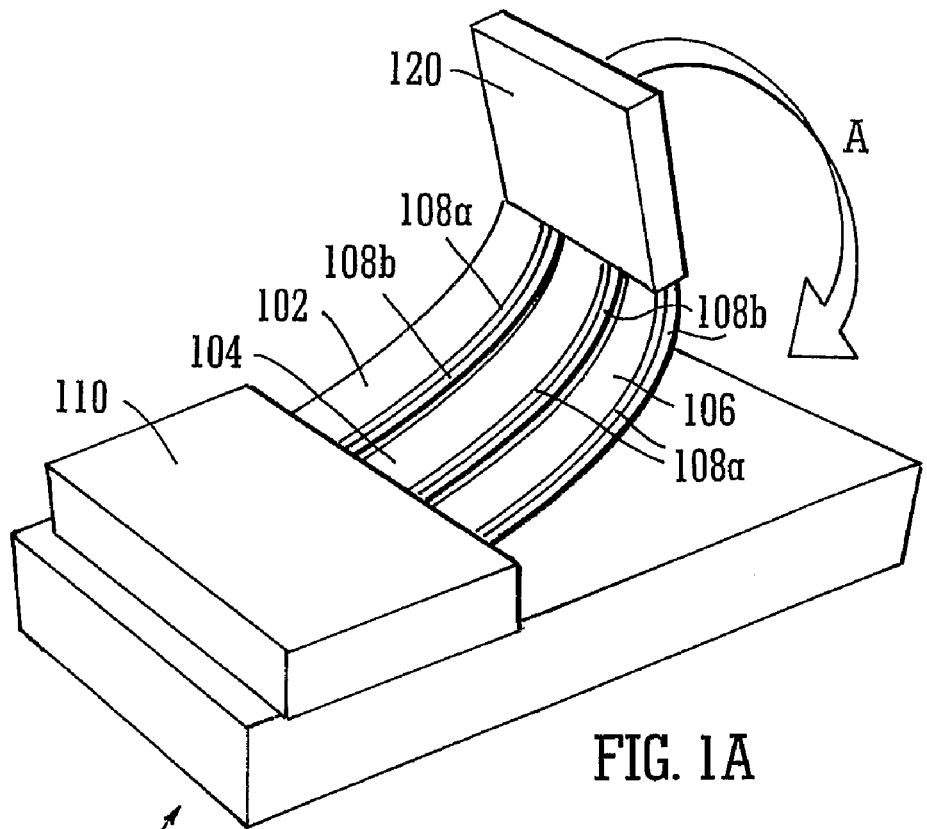
FIGS. 1A and 1B show perspective views of a device in accordance with an embodiment of the present invention, in respectively a first configuration and a second configuration.
Figure 1B:
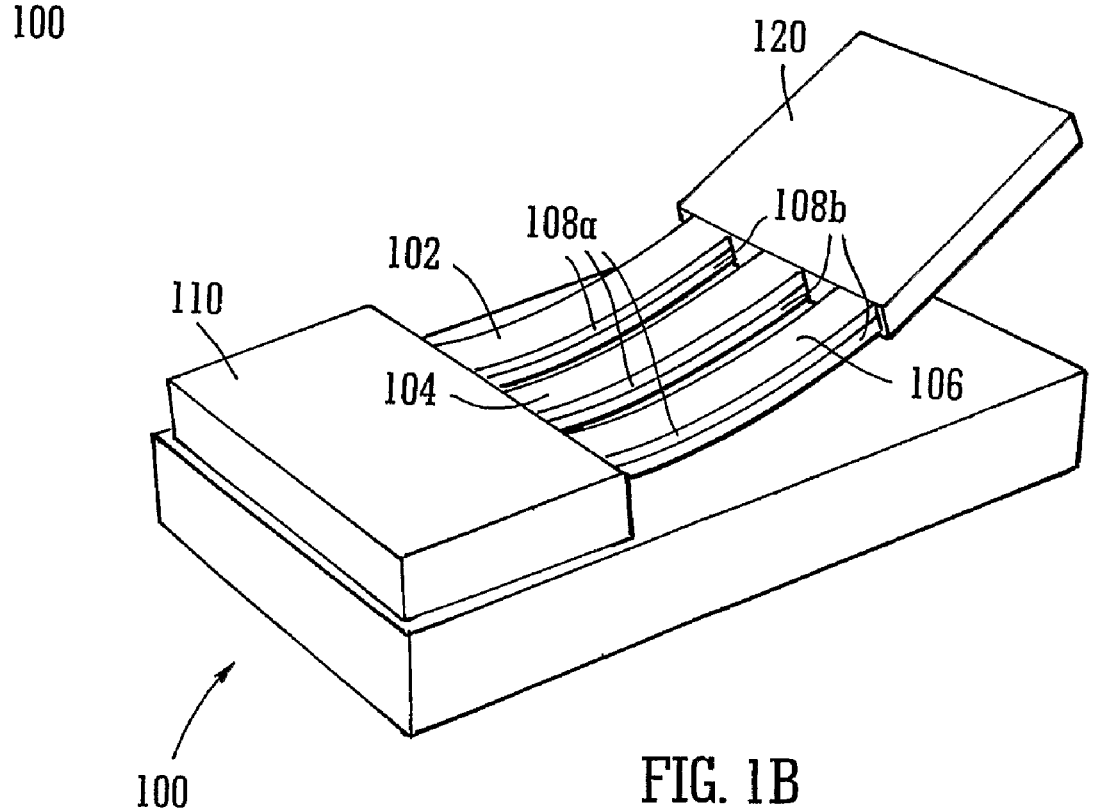
Figure 2:
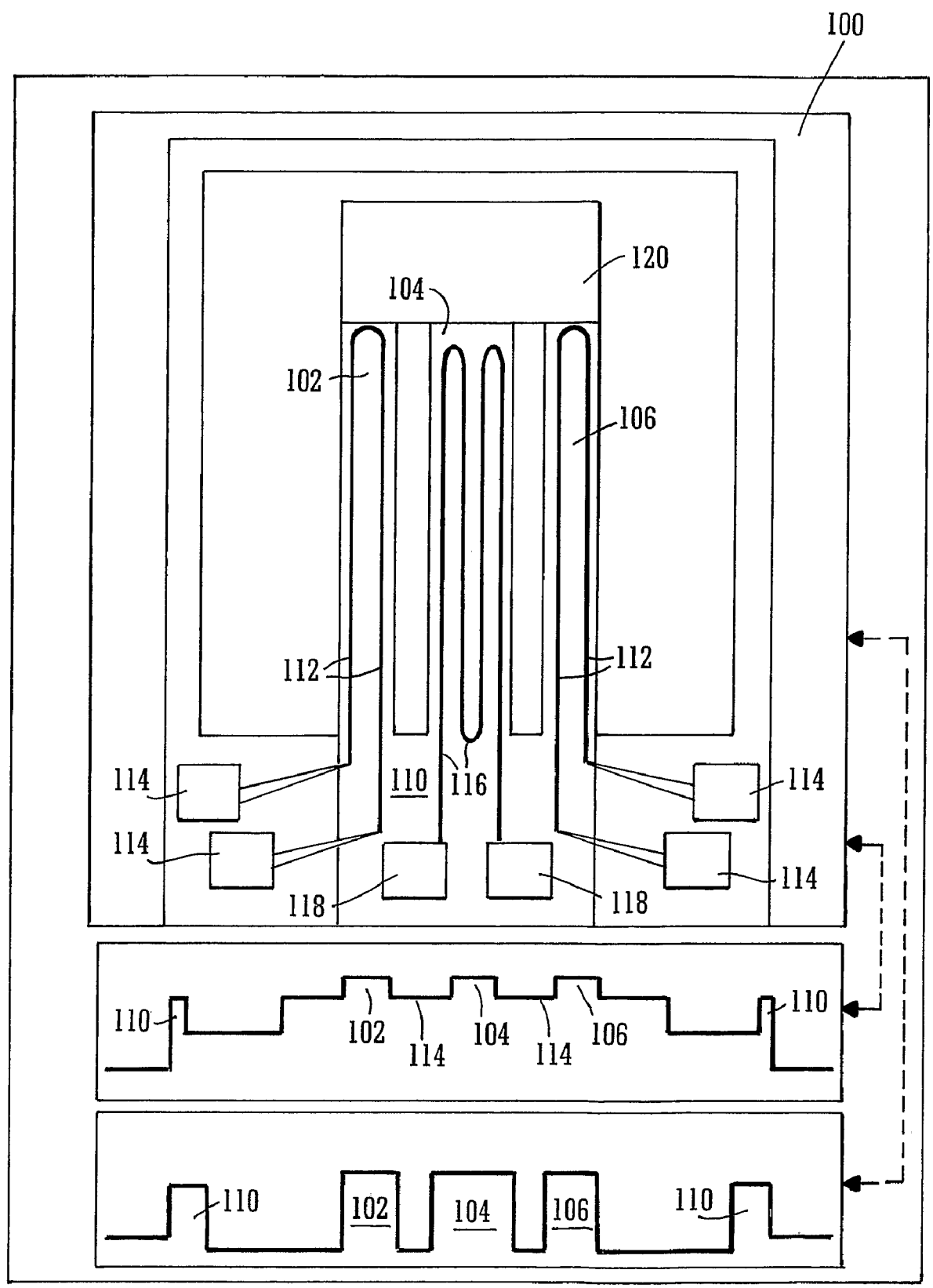
FIG. 2 shows a schematic plan view of the device illustrated in FIGS. 1A & 1B, with two profile views at different positions along the length of the device.

FIGS. 1A, 1B and 2 illustrate a device 100 for detecting the properties of fluid, in accordance with a preferred embodiment of the present invention.

The device 100 comprises three flexible elements coupled to a body region 110.

In this particular embodiment, each flexible element 102, 104, 106 is an integral part of and extends from the body region 110. The first end of each flexible element is connected to the body region 110. The second end of each flexible element, distant from the first, is free to move in relation to the body region. Each flexible element is a bar with a rectangular surface area, with the long side of the rectangle extending from the body region 110. In this particular embodiment, each flexible element 102, 104, 106 comprises a laminate of at least two layers 108a, 108b. The materials of each layer have different coefficients of thermal expansion (CTE). The layers can be formed of different materials. Alternatively, each of the layers can be formed of the same material, with that material processed in different layers (e.g. stressed and/or coupled to further materials within the flexible elements) such that the layers display different coefficients of thermal expansion. For example, stressing of the materials in different directions can lead to the thermal coefficient of expansion having directional dependence. Thus, if the different layers are formed of the same material, but with the different layers being stressed in different directions, the different layers will effectively have different coefficients of thermal expansion.

Under application of heat, one layer will expand more than the other for the same rise in temperature, and hence the flexible element being heated will bend in the direction of the material with the lower coefficient of thermal expansion. Upon cooling, one layer will contract to a greater degree than the other for the same decrease in temperature, and hence the flexible element will then bend in the direction of the material with the greater coefficient of expansion.

A respective heater element 112 is located on or within flexible elements 102, 106. Flexible elements 102, 106 are disposed either side of flexible element 104. Each of the flexible elements extend longitudinally, and are parallel.

Electrical contact pads 114 allow an electrical signal from an electrical signal generator to be applied to each heater element 112. Typically, each flexible element 102, 106 will be of similar dimensions, and be formed of similar materials. An identical signal will thus be applied to each of the heater elements 112, so as to ensure that the two beams 102, 106 are deflected to the same degree.

Each of the three beams 102, 104, 106 is of substantially the same length. A coupling member 120 is connected to each of the free ends of the flexible elements 102, 104, 106 (i.e. the ends of the flexible elements that are distant from the body region 110). The coupling member is preferably formed of a relatively rigid material. Preferably, the coupling member is formed of a thermally insulating material. In use, the coupling member (and the flexible elements) will be immersed in a fluid. Preferably, the material of the coupling member acts as a better thermal insulator than the fluid. In the particular embodiment illustrated in the Figures, the coupling member 120 is shaped as a planar element, extending in a plane away from the elements 102, 104, 106. The coupling member 120 is of the same thickness as the flexible elements 102, 104, 106. When the device is utilised, this shape allows the coupling member 120 to act as a paddle, resisting the oscillations of the flexible elements within the fluid being measured, and hence allowing tailoring of the signals (resonance, damping, etc.) for measurements in various (or varying over time) fluids.

A movement sensor 116 is located on or within central flexible element 104. The movement sensor 116 extends along the full length of the flexible element (but is not restricted to this region and can fractionally extend into the coupling member in order to sense strains at the flexible member—coupling member interface). The movement sensor is arranged to provide a signal indicative of the movement (i.e. degree of bending) of the flexible member 104. In this particular embodiment, the movement sensor 116 takes the form of a piezoresistive material. A piezoresistive material is one whose electrical resistance changes upon the application thereon of mechanical strain. The piezoresistive material can be either platinum, gold or aluminium. However, more preferably the piezoresistive material forming the movement sensor 116 is nichrome, or a chrome-copper alloy. Such materials are preferable, as they are less sensitive than platinum, gold or aluminium to changes in temperature, and thus the movement sensor will be less affected by thermal noise. Electrical contact pads 118 are coupled to either end of the electrical track of piezoresistive material forming the movement sensor 116. In use, a resistance-measuring device is utilised to measure the change in resistance across the pads 118 as a function of time, so as to provide a signal indicative of the movement rate of the flexible element 104.

Figure 3:
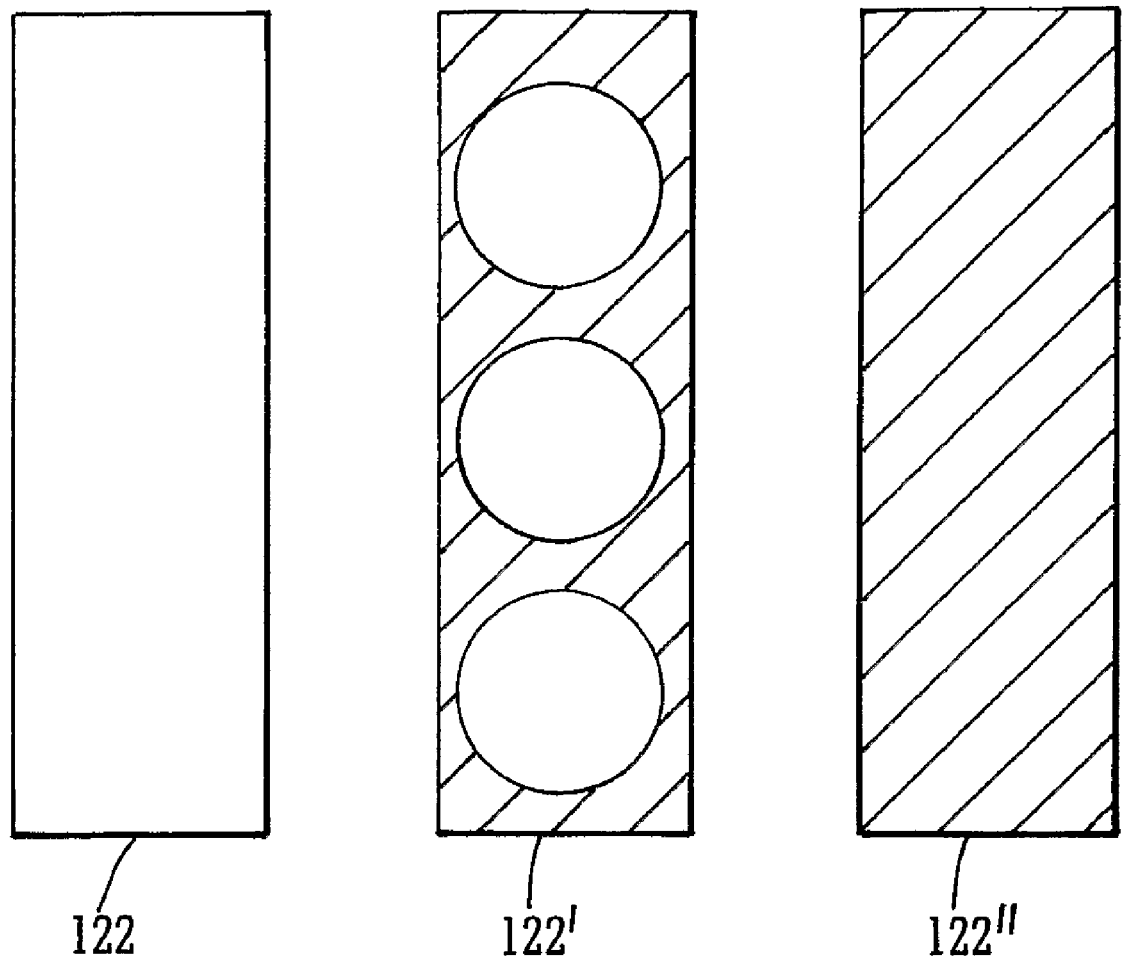
FIG. 3 illustrates three different configurations of the regions between the first and second flexible elements, showing a plan view of how the regions can take the form of a void, be partially filled, or be fully filled.

FIGS. 1A, 1B and 2 illustrate the flexible elements 102, 104, 106 are separated from the adjacent flexible element by a gap 122 of predetermined, fixed width, with only coupling member 120 coupling together the flexible elements. FIG. 3 illustrates three alternative implementations that can be utilised at the position 122 between the flexible elements. Firstly, the region 122 between the flexible elements 102, 104, 106 can take the form of a void (i.e. filled with the fluid in which the flexible element is immersed, including liquid or air). It will be appreciated that, although the region 122 as shown as being generally rectangular due to the bar-shape of the surrounding flexible elements, in other implementations, the region 122 can be of any shape e.g. circular, ellipsoid, diamond, square or arbitrary. Alternatively, as shown by 122', the region can be partially filled by another material (the circles indicate the remaining voids/air gaps passing through the region, and open to the surrounding environment). The apertures extending through the region 122' can be circular as indicated within FIG. 3, or can be any other shape. Alternatively, as indicated by 122", the region can be fully filled by a material. If the region 122 is fully filled by a material (thus acting as a paddle), then preferably that material has similar mechanical properties to the materials of the flexible elements. If required, the rigidity of the paddle can be further regulated by the thickness of the structural layer forming the paddle such that the material will flex to a similar degree as the flexible elements or remain relatively firm. The material located between the flexible members (i.e. in 122', or 122") can act as an additional coupling member, or can take the place of the coupling member 120. Preferably, the material is an insulative material e.g. a thermally insulative material and/or an electrically insulative material, depending upon the characteristics of the actuating portions of the flexible elements. For example, as the actuation of the device described above is caused by operation of the heater elements 112, then preferably any material extending between the elements (e.g. in gap 122, or forming coupling member 120) comprises a thermal insulator. Preferably, the material acts as at least as good a thermal insulator, if not a better thermal insulator, than the flexible elements.

In use, the flexible elements 102, 104, 106 (and the coupling member 120 that acts as a paddle) are immersed in a fluid. An actuating signal is applied to flexible members 102, 106. The actuating signal takes the form of an electrical signal being applied to the heater element tracks 112 (via electrical contact pads 114). Heat is dissipated due to electrical resistance in the tracks 112, which causes the temperature of the flexible elements 102, 106 to increase. Thus, one layer of the laminate 108*a* will expand at a greater rate than the other 108*b* due to the differential in the respective coefficients of thermal expansion. FIG. 1A shows the bent position of the flexible elements when no heat signal is applied. As the heat signal is applied, flexible elements 102, 106 (but not 104) are heated by the tracks 112 embedded therein, leading to a change in configuration of the flexible elements i.e. the elements bend. Due to the particular arrangement of the layers having different coefficients of thermal expansion, in this particular embodiment the flexible elements 102, 106 will bend to the position illustrated in FIG. 1B i.e. the elements bend and become straighter/more linear (less curved). Preferably, the ends of the flexible elements 102, 106 (to which the coupling member 120 is attached) move through a distance within the range 20 to 650 µm, with the second ends preferably moving at least 100 µm. As the free (second) ends of the flexible elements (i.e. the ends not connected to the body region 110) are coupled together, movement of the flexible elements 102, 106 also causes a corresponding movement/bending of the passive flexible element 104.

In bending, flexible element 104 induces a strain on the piezoresistive element 116 that results in a change in its electrical resistance. Hence, the resistance of the movement sensor 116 indicates the movement of the sensing element 104. This resistance can be measured by any resistance measuring device or circuit, including, but not limited to, a Wheatstone bridge.

For a given input signal to the heater elements 112, the flexible elements 102, 104, 106 will move (or deflect) a predetermined amount. If the heat signal is repetitive, e.g. a sinusoidal signal or a train of square pulses, then the flexible element will continue to bend when it is heated, and will relax towards its equilibrium position when no (or less) heat is applied. Thus, the flexible elements 102, 106 (and hence flexible element 104) can be made to oscillate. Alternatively, a single actuation pulse (i.e. one shot or 'step function excitation' induced by e.g. a large and short electrical pulse) can cause the flexible elements to produce a 'ringing' response (e.g. see FIGS. 4A-C). If a damping force is applied that opposes the movement of the flexible elements, such as if the flexible elements are moving through a viscous medium, the degree of deflection and rate of change of deflection of the flexible elements will be affected. Thus, measurement of the amplitude of deflection, and/or the rate of change (or phase) of deflection compared to the signal used to drive the flexible elements 102, 106, can be used to detect and determine the viscosity of a fluid in which the flexible elements are immersed.

Figure 4A:
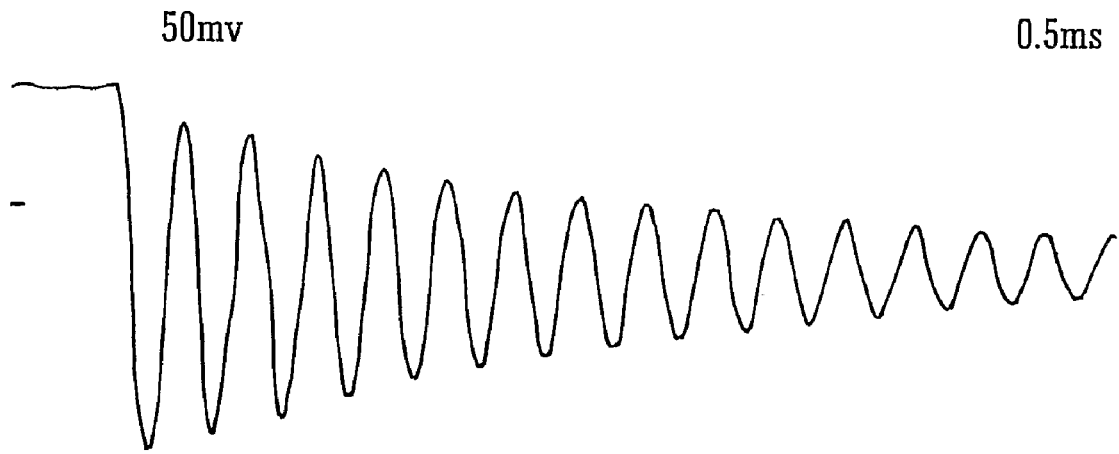
FIGS. 4A, B and C illustrate the different responses of a sensor in a device in accordance with an embodiment of the present invention in respectively air, water and silicone oil.
Figure 4B:
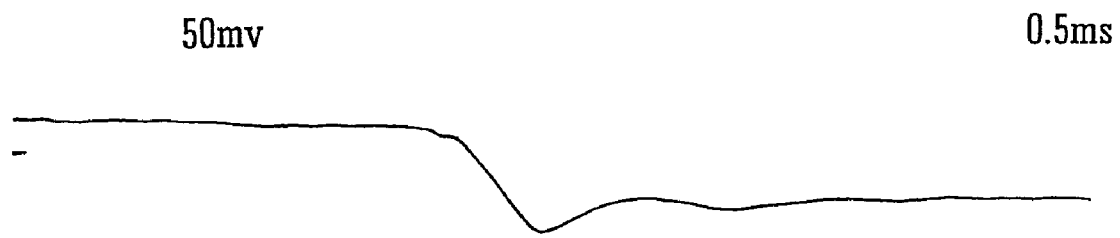
Figure 4C:
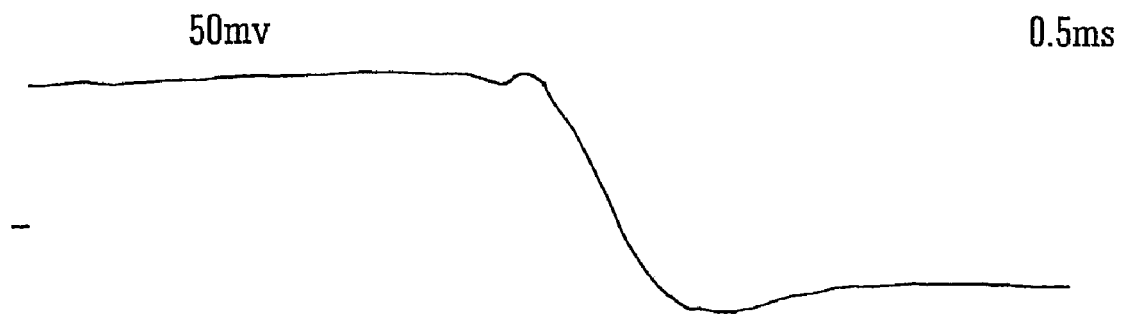

WO2005/054817, which is incorporated herein by reference, describes how such viscosity measurements (and measurements of other properties or fluid) can be made. Similar measurements can be made using the device described herein. Thus, the signal from (change in resistance of) the movement sensor can be processed to determine a value indicative of at least one property of a fluid. This can be done, for example, by determining a rate of change of movement of the flexible element 104, by monitoring a change in the signal with time and determining a value indicative of the viscosity of a fluid from the rate of change of movement. Alternatively, the amplitude of the deflection of the flexible element, the resonant frequency or "ringing" of the flexible element (which is proportional to the applied heat signal) can be processed to determine a value which is indicative of the viscosity of the fluid in which the flexible elements are immersed. For example, FIGS. 4A, 4B and 4C show the change in resistance of the movement sensor as a function of time in different fluids (respectively air, water and silicone oil) after a single heat pulse has been applied to deflect the flexible elements from their rest position (shown in FIG. 1A). As can be seen, the more viscous the medium, the more pronounced the damping effect experienced by the flexible elements.

Preferably, the device is utilised to measure the viscosity change with time in a fluid. For example, the change in viscosity of blood can be measured as a function of time, as the blood coagulates for example, measurements can be performed at predetermined intervals to determine the viscosity of blood/relative change in viscosity of the blood with time. Preferably, the volume of fluid from which the properties are being measured is of the order of one microliter e.g. up to 5 microliters, or more preferably between 0.5 and 3 microliters. Preferably, the device is arranged to measure a range of viscosities that are suitable for blood measurements e.g. a range of viscosity from 1 cP-1000 cP.

As the actuating portion is provided in an element separate from the movement sensor, the movement sensor is less affected by noise caused by actuation of the flexible elements. Thus, the accuracy of the sensor can be improved. Further, providing a coupling member 120 shaped to act as a paddle or oar increases the influence of the viscosity upon the movement of the flexible element, allowing an increase in sensitivity.

It will be appreciated that the above embodiment is described by way of example only, and that various alternatives will be apparent to the skilled person as falling within the scope of the appended claims.

For example, although in the above embodiment two flexible elements 102, 106 are actuated to move, and a single flexible element is utilised to detect movement, it will be appreciated that alternative configurations could be used. For example, a single actuator flexible element and a single movement sensor flexible element could be implemented. Alternatively, any number of movement sensor flexible elements and actuator elements could be implemented e.g. the elements could be formed as an array.

In the preferred embodiment, only the actuator flexible elements 102, 106 include an actuating portion arranged to cause deflection of the flexible elements, and only the sensor flexible element 104 includes a movement sensor. However, it will be appreciated that any of the flexible elements could include both a movement sensor and an actuation portion. For example, two flexible elements as described within WO2005/054817 could be coupled together, and operated in accordance with an embodiment of the present invention. In particular, only one of the flexible elements would be actuated to move (causing a corresponding movement in the other flexible element to which it is coupled), with only that other flexible element being utilised to sense movement.

In the above embodiment, the coupling member 120 has been illustrated as being a planar member. In alternative embodiments, the coupling member can take the form of a paddle or plate that is perforated to alter fluid drag and/or shear within the fluid of interest. For example, perforations in the coupling member may be provided, so as to enhance the coagulation of the fluid being monitored, thus allowing a measurement of the viscosity change in the fluid over a relatively short time period. Such a coupling member would be particularly suitable for monitoring the change in viscosity with blood over time. It will be appreciated that equally, the apertures in the coupling member could be provided so as to affect the chemical and/or physical reactions.

If the flexible elements are to be utilised to monitor a fluid containing discrete particles or droplets/colloidal particles, then any apertures can be provided so as to be any of: a similar size to the particles, be much greater than the particles, or be much smaller in size than the particles. For example, if the evolution of a colloidal suspension is being monitored, then the size of the apertures may be provided so as to be generally of a similar size to the intermediate particles in the suspension; smaller colloidal particles will pass through the apertures, whilst larger particles will not, and similar size particles may remain trapped within the apertures. Such a system can thus provide more information on the evolution of the colloidal suspension, as the flexible elements movement is monitored over time. Equally, it will be appreciated that other configurations/shapes of the coupling member can be utilised to enhance such shear or drag effects. The size of the coupling member will directly influence mechanical time constants of the bimorph construction, and thus alter the amplitude and time constants associated with the sensor response. Typically, the coupling member will extend away from the flexible elements by a distance of at least 20%, and more preferably 50% of the length of each flexible element. Typically, the length of the flexible element from the body region to the coupling member is between 100 and 1000 µm. Although the coupling member has been indicated as a paddle extending from the ends of the flexible elements, in other embodiments the coupling member can take the form of one or more discrete members extending between the flexible elements e.g. extending across the area 122 between the flexible elements.

In the above embodiment, the coupling member has been described as being formed of a thermal insulator, with the flexible elements being thermally actuated. In other implementations, the flexible elements may be actuated via electrostatic, forces magnetic forces or electrically (e.g. using a piezovoltaic material). In such alternative implementations, the coupling member will be formed of an appropriate insulative material e.g. if the actuation is electric, then the coupling member will be formed of electrically insulative material.

In the above embodiment, the actuation of the flexible elements to move is caused by heating. However, it will be appreciated that other actuation systems could be used. Similarly alternative movement sensors could be utilised other than utilising a piezoresistive track. For example, a piezoelectric element could be utilised as either a movement sensor or an actuating portion, depending whether an electrical signal is measured from the piezoelectric material, or applied to the piezoelectric material. WO2005/054817 describes various sensors, actuators and types of construction, any of which can be utilised for different embodiments of the present invention.

Typically, the flexible elements will be formed of a laminate comprising one layer of either a polymer (from a group consisting of polyimides, polyamides and acrylic polymers), or another type of material such as gold, aluminium, copper, or silicon dioxide. Preferably, the material is an insulating material.

The other layer of the laminate may comprise a metal, such as gold, aluminium or platinum as described above, and is most preferably a material with higher rigidity (Young's Modulus) than the first laminate and sufficient elasticity (Elongation) to sustain the deformations caused by the first laminate (in the region of 20 μm-650 μm). The actuation portion (heaters) in flexible members 102 and 106 can be made from any conductive material (e.g. metals, or conductive polymers) whilst the sensing portion in element 104 should be made from the material group with sufficient piezoresistive or piezovoltaic properties. Typically, in the above described embodiment, the sensing portion is made from Au or Pt but could also be made from conductive polymers, and, preferably from NiCr or CrCu alloys. Any conductive layers or tracks in members 102 and 106 should preferably not extend into the coupling/connection member 120.

It will be appreciate that other materials can be utilised to fabricate the flexible elements, the coupling member, and any thermally insulative region located between adjacent flexible elements. Tables 1 and 2 illustrate the properties of suitable materials for use in such a construction. In Table 2, air, alcohol and water are listed, as examples of the potential thermal properties of the fluids that may fill the regions 122 between the flexible elements, if the regions 122 are not otherwise filled by another material.

In the above embodiment, the flexible elements 102, 104 and 106 are described as all having a similar, laminate structure. However, it will be appreciated that different materials could be utilised to form the different flexible elements i.e. the sensor flexible element could be formed of different materials, or have a different configuration, than the movement flexible elements 102, 104. However, it is desirable that the flexible elements each have a similar degree of elasticity (e.g. Young's modulus) such that all of the flexible elements flex or bend to a similar degree, as the movement flexible elements are actuated.

The preferred combination of structural materials for the laminates of members 102, 104 and 106 from Table 1 below are—i) Polyimide-Au and ii) Polyimid-Polyimide in which case the two different types of polyimide with large CTEs difference are used and with at least one of the laminates having a more rigid structure (e.g. Young's Modulus>5 GPa). Another possible combination is iii) Polyimide-Al but with lower efficiency due to a higher CTE of Al. Polyimide is preferred because of its high CTE and very low thermal conductivity and capacity (thermal insulator). Gold on the other hand has got excellent mechanical properties (elastic but rigid compared to polyimide) and relatively lower CTE. Higher thermal conductivity is desirable when fast responses of flexible members are required. If alternative activation methods are chosen, thermal parameters are of lesser interest. Finally, a careful selection of polyimides (or any suitable polymer material) can yield best performances both thermally and mechanically. Possible laminate combinations include Al—Si, Al—SiO2, Polyimide-Si, and Polyimide-SiO2.

TABLE 1

Comparison Table for Materials for use in microfabrication processes

| | Density [Kg/m$^3$] | Resistivity [Ωm] | Young's Modulus [Gpa] | Coefficient of Thermal Expansion* [$10^{-6}$/K] | Thermal Conductivity [W/mK] |
|---|---|---|---|---|---|
| Gold (Au) | 19280 | $2.2 * 10^{-8}$ | 80 | 14.1 | 315 |
| Aluminium (Al) | 2700 | $2.67 * 10^{-8}$ | 70 | 23.2 | 237 |
| Chromium (Cr) | 7190 | $13.2 * 10^{-8}$ | 140 | 8.2 | 90.3 |
| Nickel (Ni) | 8910 | $6.9 * 10^{-8}$ | 200 | 12.7 | 90.5 |
| Copper (Cu) | 8960 | $1.7 * 10^{-8}$ | 128 | 16.8 | 398 |
| Silicon Bulk (Si) | 2330 | $2.3 * 10^3$ | 127 | 2.5 | 80-157 |
| PolySilicon | 2330 | $2.3 * 10^3$ | n/a various | 2.3 | 80-157 |
| Silicon Nitride (Si$_3$N$_4$) | 3100 | $>10^{11}$ | 150-380** | 2.2-2.9 | 30 |
| Silicon Dioxide (SiO$_2$) | 2200 | $10^{16}$ | 75 | 5.8 | 1.4 |
| Polyimide | 1610*** | N/A | 0.3-15***** | 6-250 | 0.155 |
| Ceramic (AlN) | 3250 | $2 * 10^9$ | 260-350$^2$ | 4.4-5.3 | 30.1 |
| Platinum (Pt) | 21440 | $10.6*10^{-8}$ | 170 | 8.9 | 73 |

*CTE is temperature dependant and the values presented here correspond to room temperature
**This parameter largely depends on the type of deposition and on process parameters such as temperature, pressure, etc.
***Varies with different polyimide families
****This parameter largely depends on the curing temperature and time as well as polyimide chemistry

TABLE 2

Thermal properties of Polyimide and other relevant materials

| | Thermal Capacity | Thermal Conductivity | Thermal Diffusivity |
|---|---|---|---|
| Gold | 0.5944 [Cal/cm$^3 \cdot °$C.] | 0.7600 [Cal/s $\cdot$ cm $\cdot °$C.] | ~1.293 [cm$^2$/s] |
| Chromium | 0.8783 [Cal/cm$^3 \cdot °$C.] | 0.2247 [Cal/s $\cdot$ cm $\cdot °$C.] | ~0.2558[cm$^2$/s] |
| Aluminium | 0.5805 [Cal/cm$^3 \cdot °$C.] | 0.5664 [Cal/s $\cdot$ cm $\cdot °$C.] | ~0.9757[cm$^2$/s] |
| Silicon | 0.3929 [Cal/cm$^3 \cdot °$C.] | 0.2868 [Cal/s $\cdot$ cm $\cdot °$C.] | ~0.73 [cm$^2$/s] |
| Alumina | 0.0279 [Cal/cm$^3 \cdot °$C.] | 0.0717 [Cal/s $\cdot$ cm $\cdot °$C.] | ~0.084 [cm$^2$/s] |
| PolyImide | 0.4186 [Cal/cm$^3 \cdot °$C.] | 0.00037 [Cal/s $\cdot$ cm $\cdot °$C.] | ~0.00088 [cm$^2$/s] |
| Water at 20° C. | 1 [Cal/cm$^3 \cdot °$C.] | 0.0014 [Cal/s $\cdot$ cm $\cdot °$C.] | ~0.0014 [cm$^2$/s] |
| Alcohol, ethyl | 0.000319 [Cal/cm$^3 \cdot °$C.] | 0.0004063 [Cal/s $\cdot$ cm $\cdot °$C.] | ~1.2737 [cm$^2$/s] |
| Air at 20° C. | 0.000289 [Cal/cm$^3 \cdot °$C.] | 0.000057 [Cal/s $\cdot$ cm $\cdot °$C.] | ~0.19706 [cm$^2$/s] |

A method of manufacture for a flexible element, such as a bimorph cantilever, will now be described with reference to FIGS. 5A-5Q.

Figure 5A:
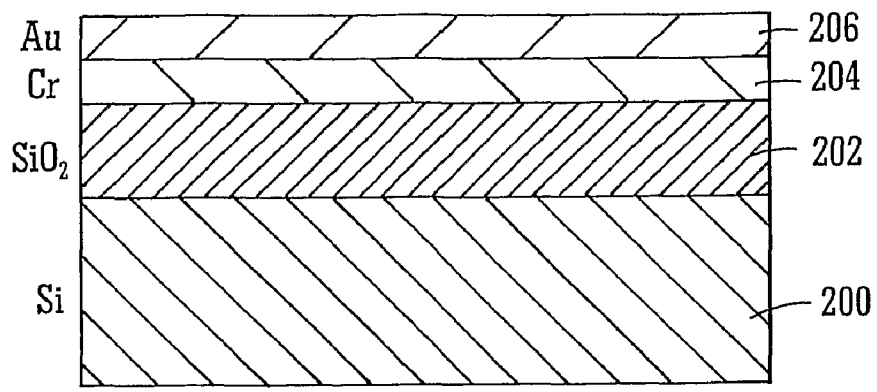
FIGS. 5A-5Q illustrate a method of manufacture in accordance with an embodiment of the present invention.
Figure 5B:
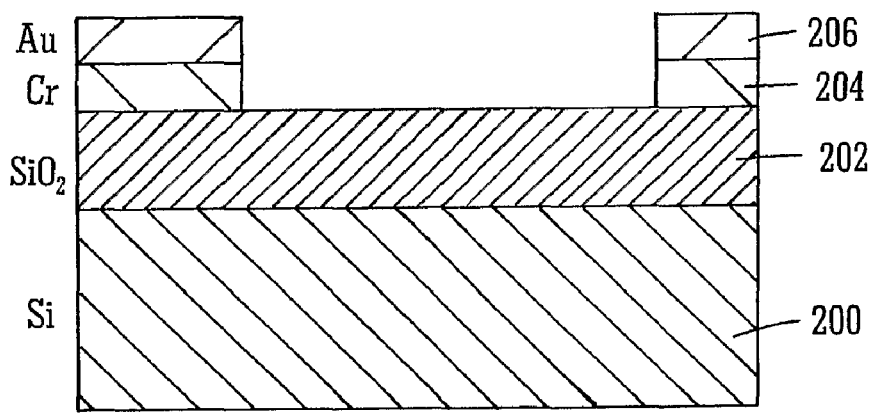
Figure 5C:
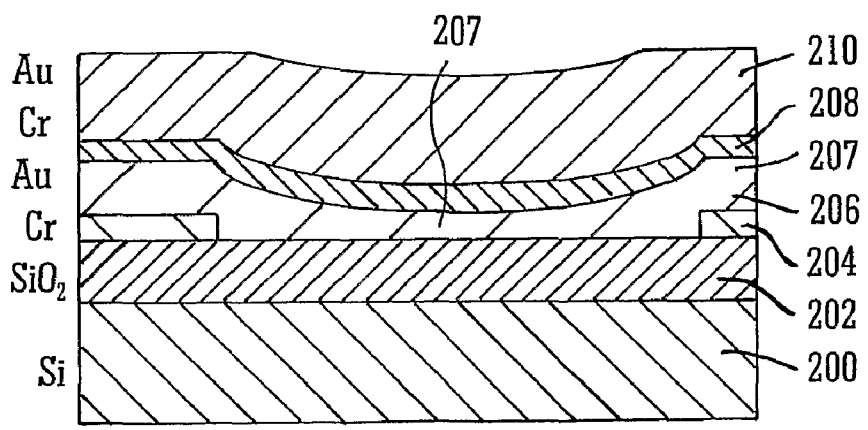
Figure 5D:
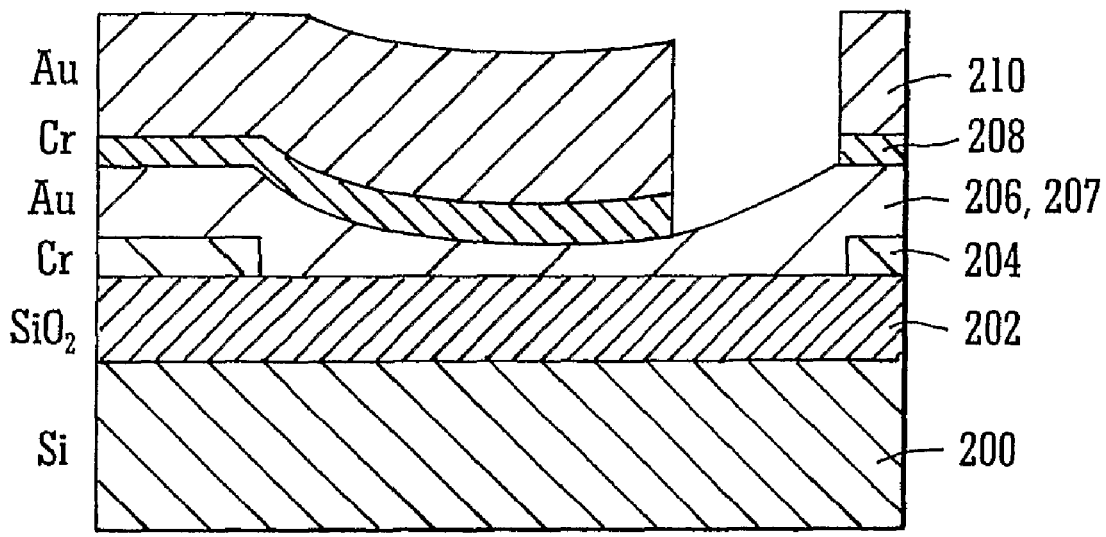
Figure 5E:
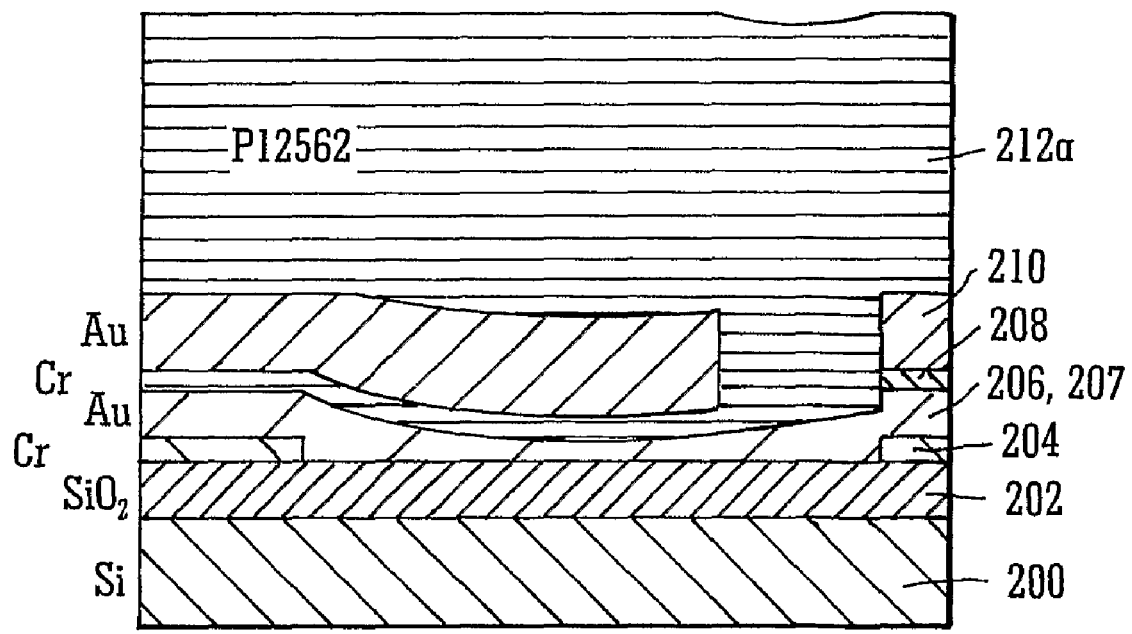
Figure 5F:
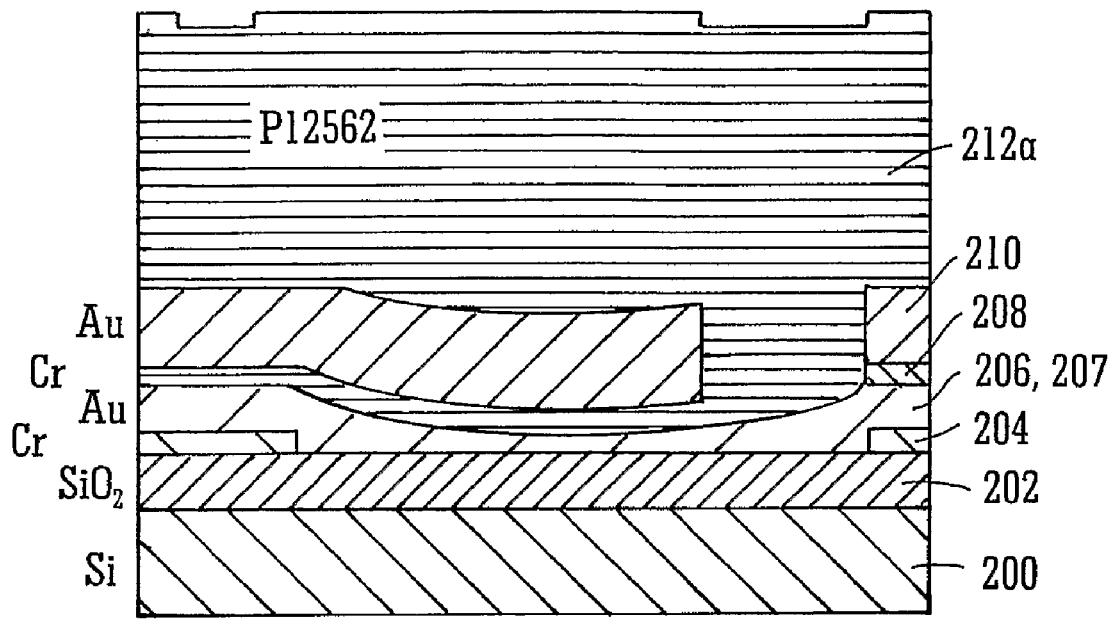
Figure 5G:
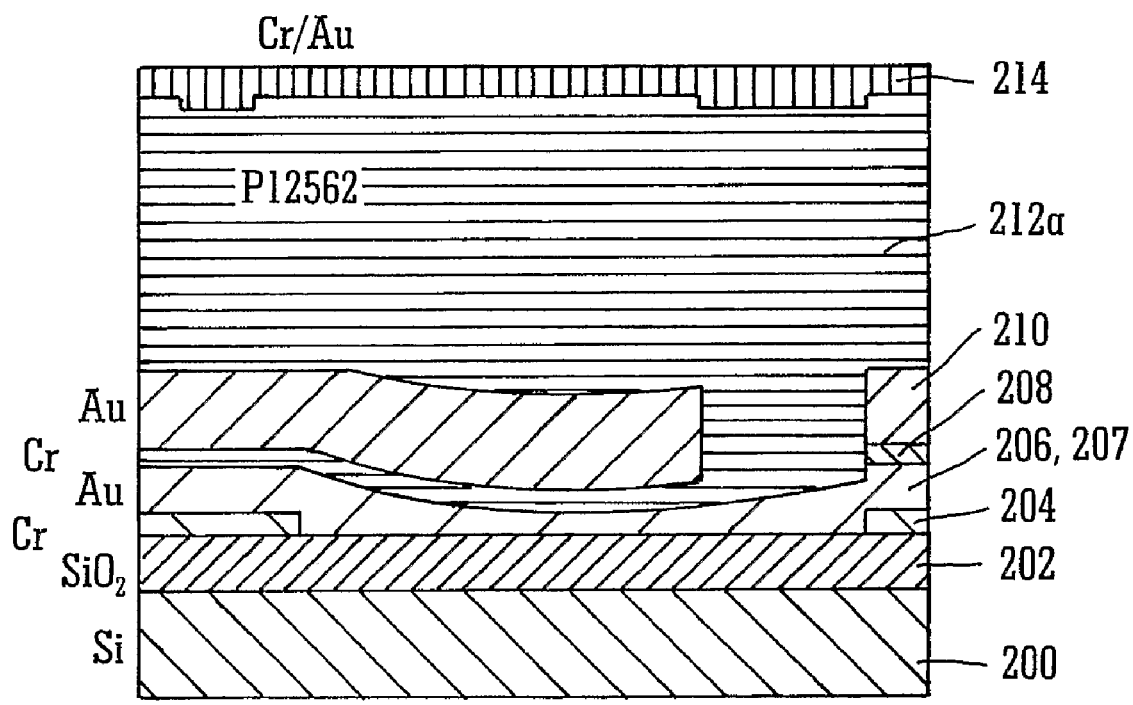
Figure 5H:
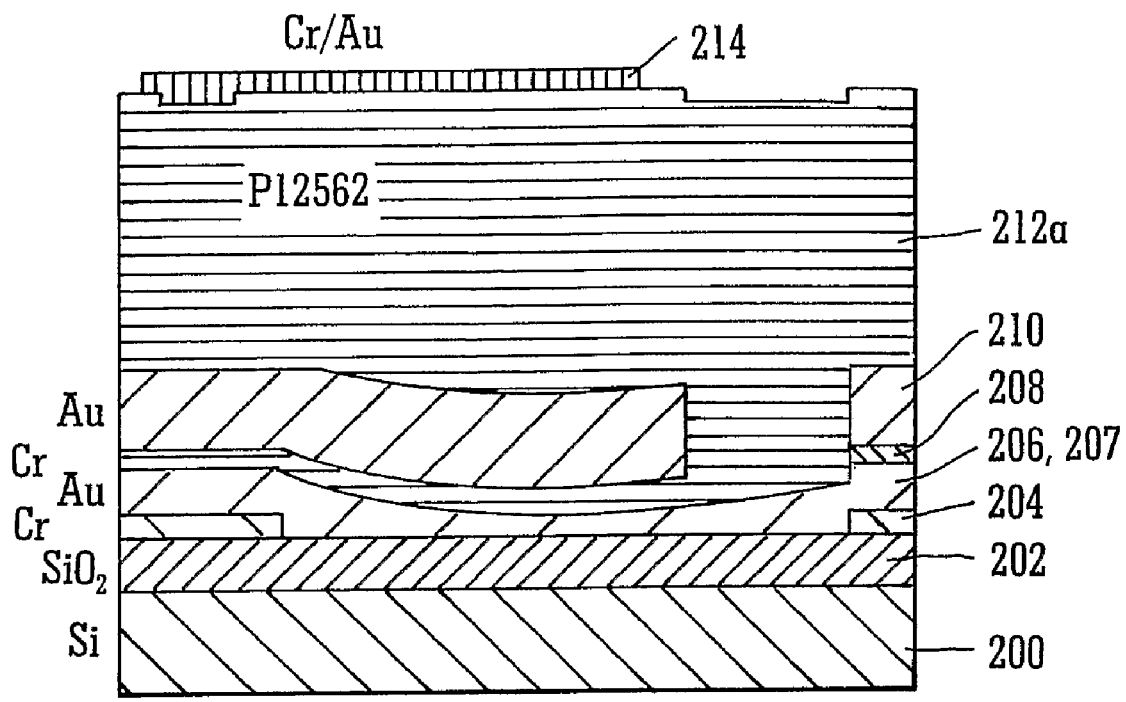
Figure 5I:
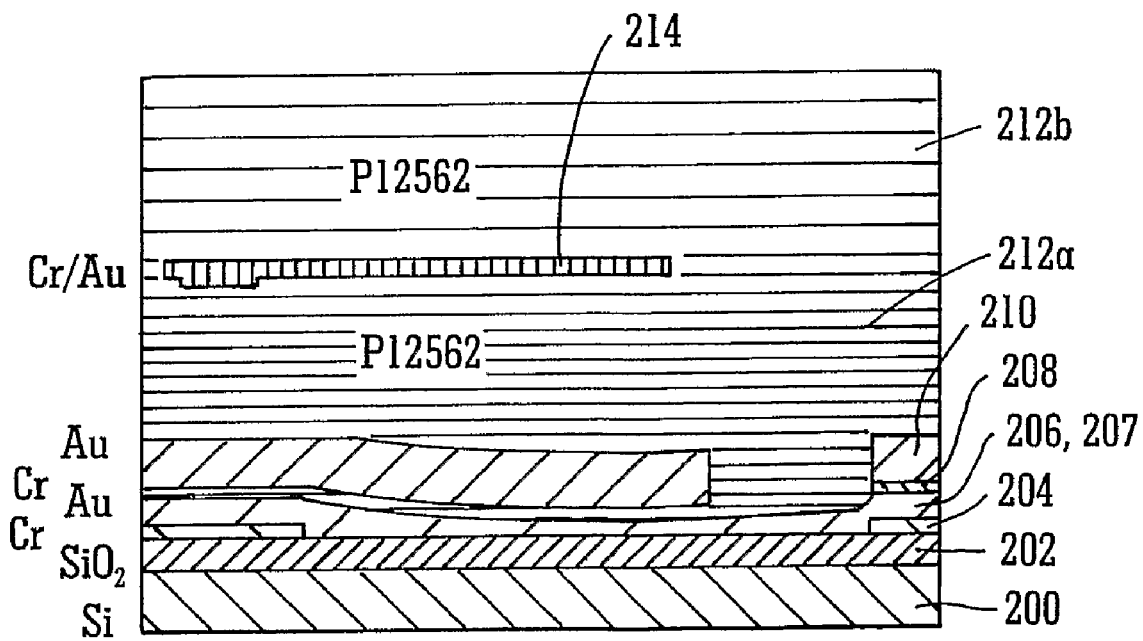
Figure 5J:
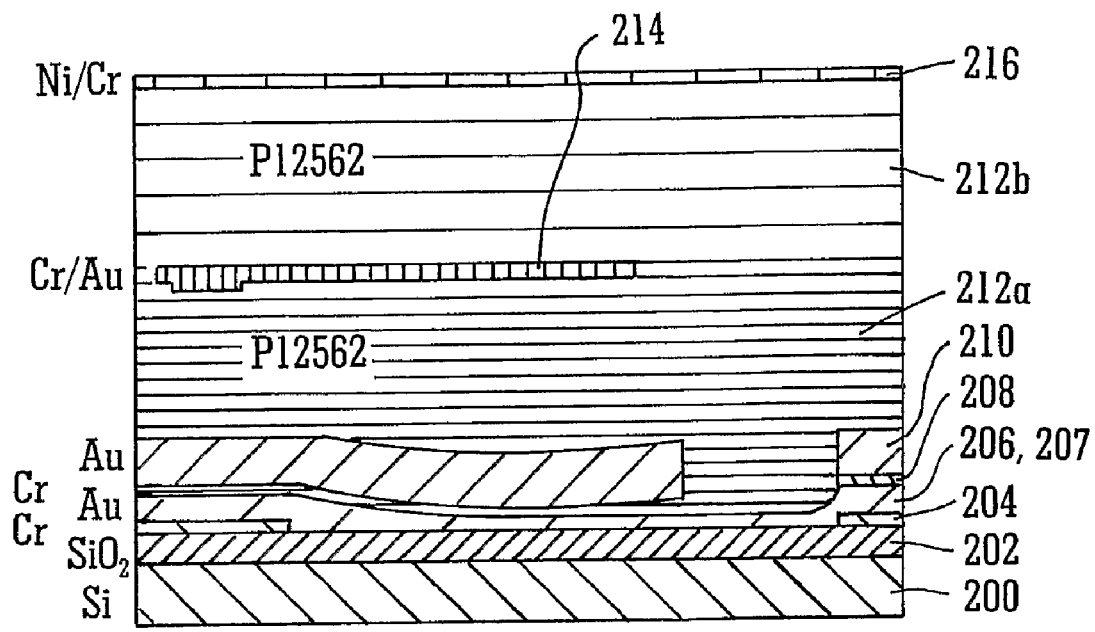
Figure 5K:
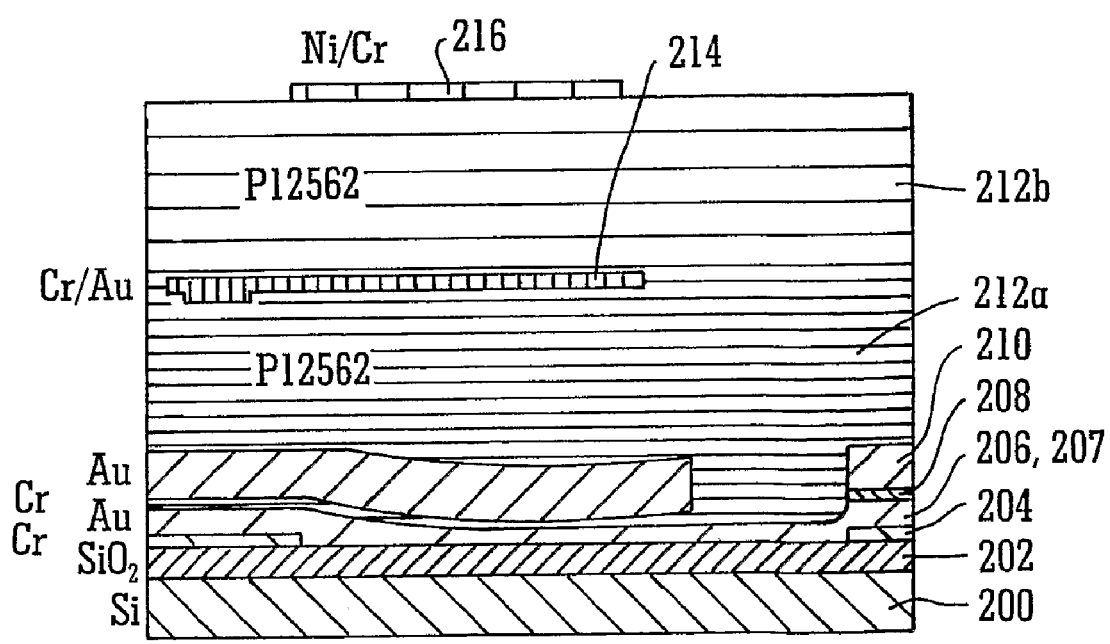
Figure 5L:
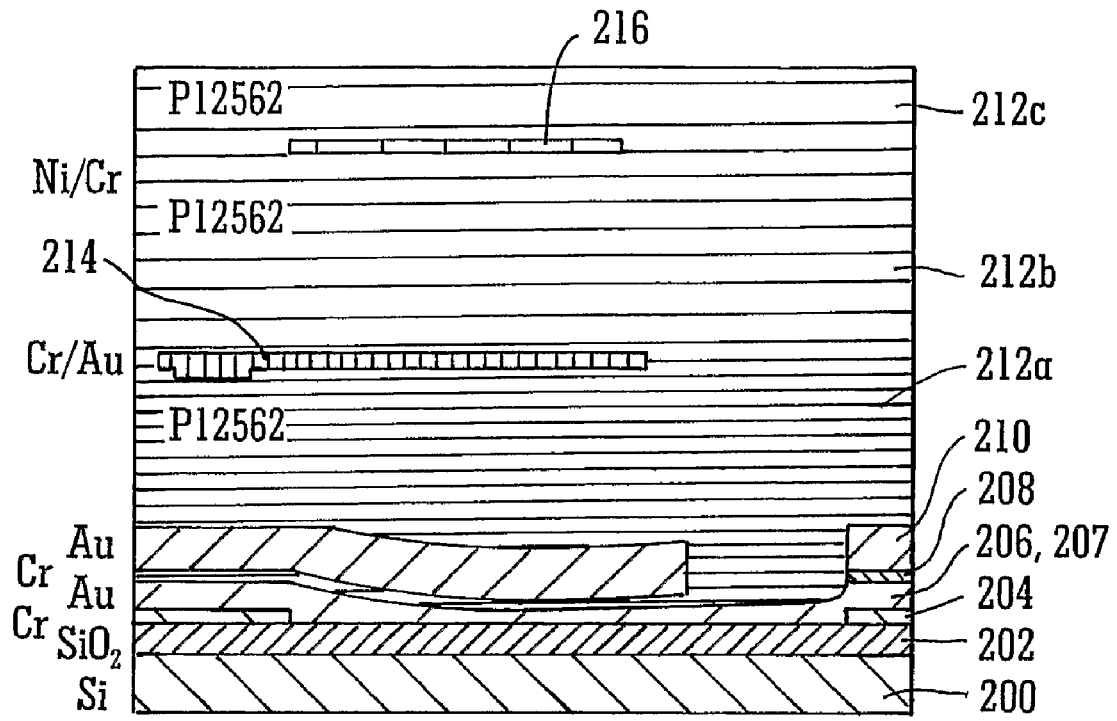
Figure 5M:
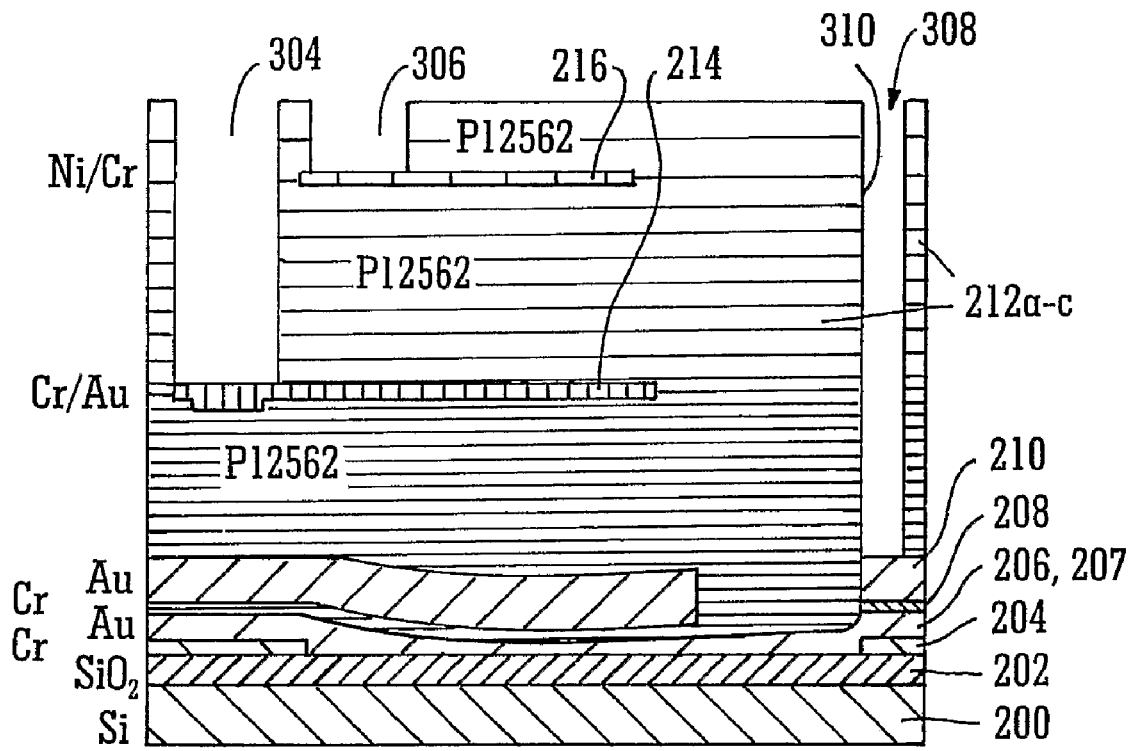
Figure 5N:
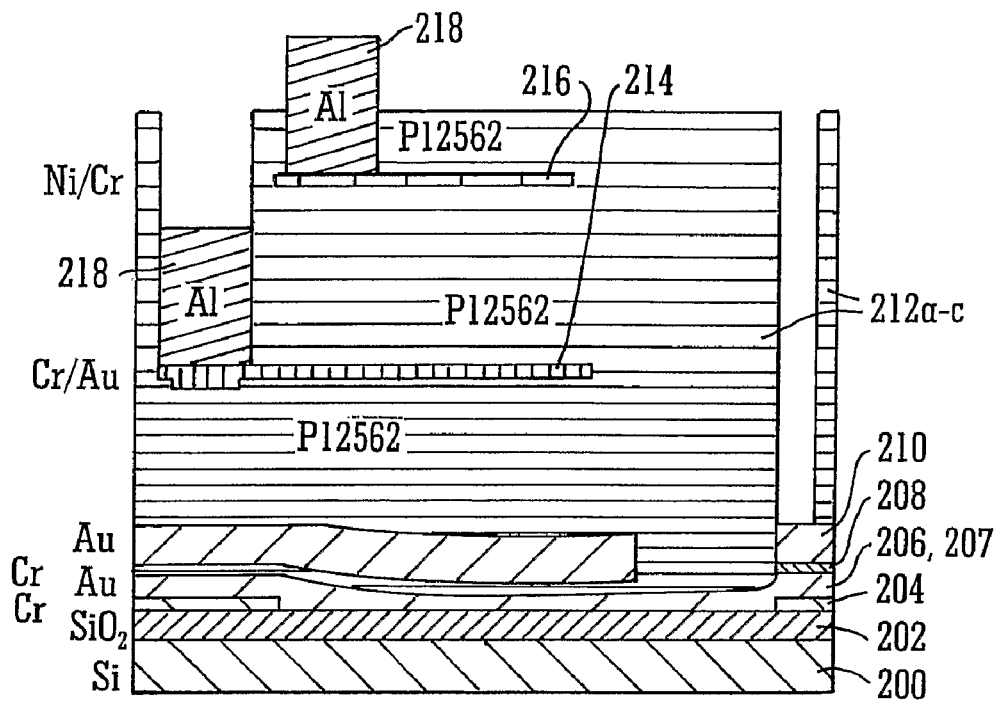
Figure 5O:
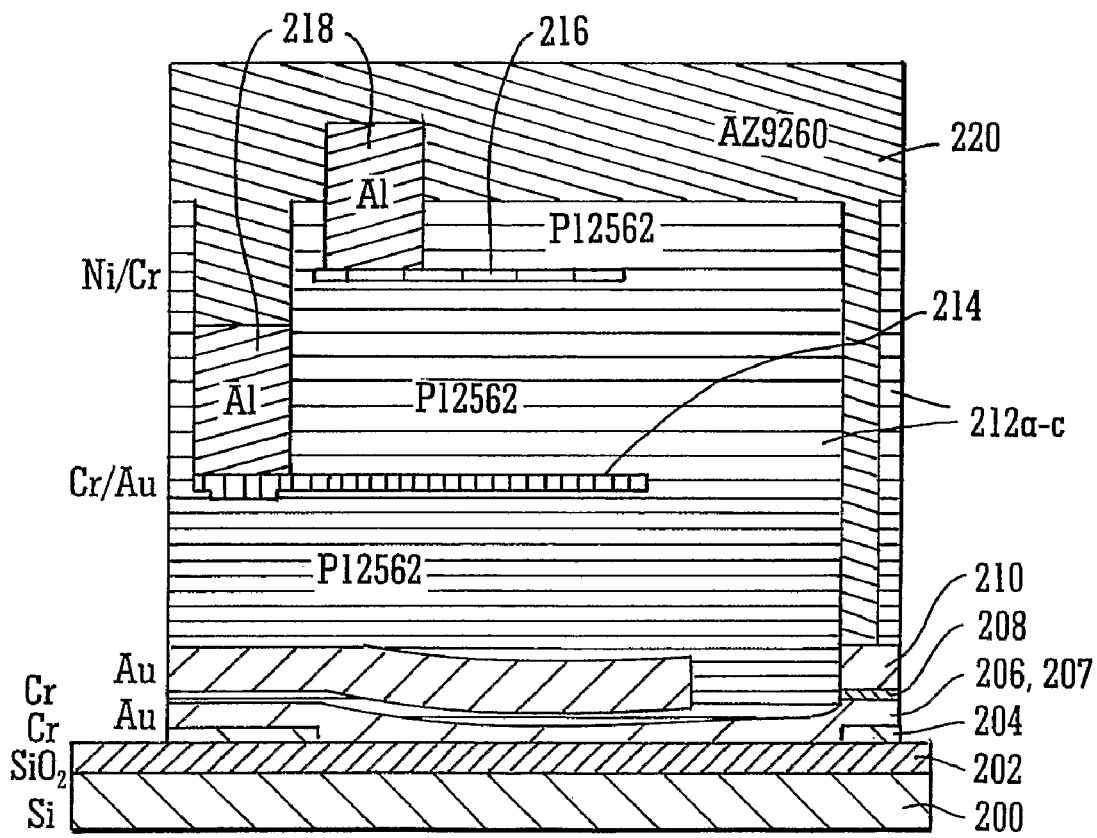
Figure 5P:
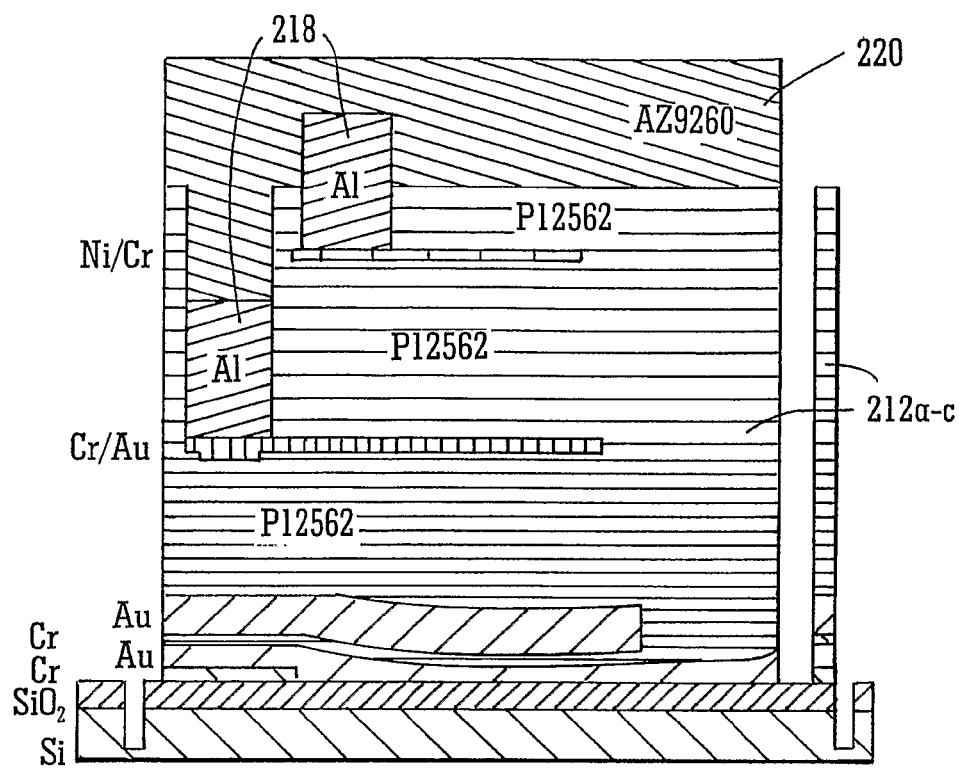
Figure 5Q:
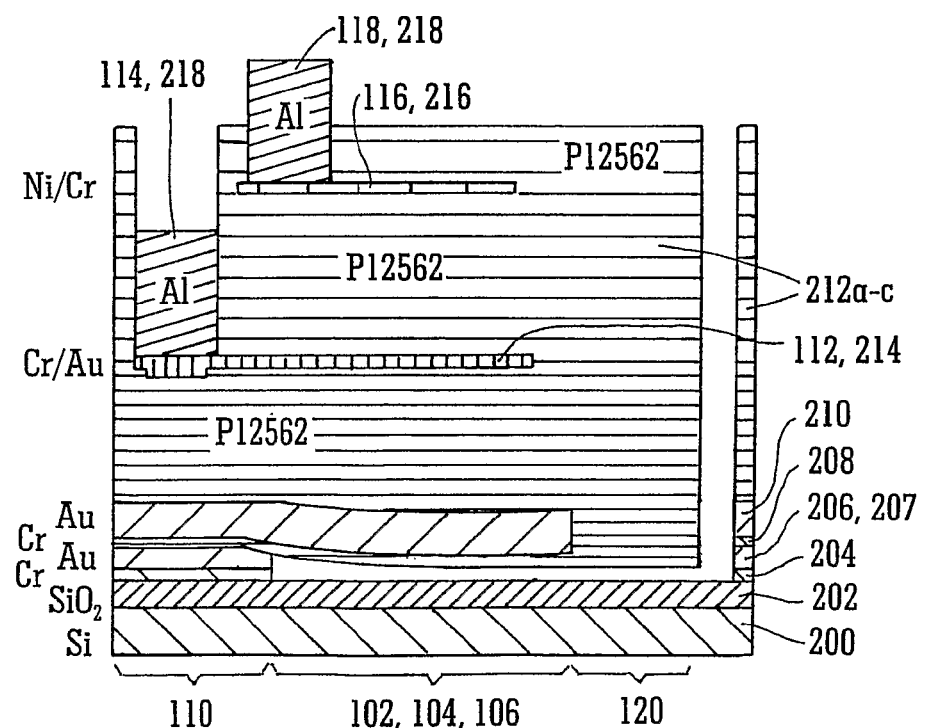

FIGS. 5A-5Q are cross sectional views illustrating a microfabrication process sequence for manufacturing a device including at least one flexible element e.g. the device illustrated in FIGS. 1A, 1B and 2. The Figures illustrate the cross section along the length of the flexible element i.e. from the body region 110 up to and including (and slightly beyond) the coupling member 120. FIG. 5Q illustrates how the different sections formed in the fabrication process correspond to the elements of the device 100 illustrated in FIGS. 1A, 1B and 2.

It should be appreciated that the cross sections are effectively transparent views i.e. it is not a cross section along any particular line through the device, but merely a view looking sideways at the device, showing all the relevant features within the different layers. It should be appreciated that such layers do not, in most instances, extend across the full width of the device. For example, in 5Q, the nickel/chromium alloy forming the movement sensor track 116 is indicated; it will be appreciated that this track simply extends within the sensor flexible element 104, and not the adjacent movement flexible elements 102, 106 (as shown by FIG. 2).

Further, it should be appreciated that the height of the different layers is exaggerated within the Figures (compared with the length) for purposes of clarity. The total thickness of the flexible elements is typically between 1 μm and 30 μm, i.e. the thickness is preferably at least an order of magnitude less than the typical length of each flexible element.

FIG. 5A illustrates the prepared wafer 200. Typically, the wafer will be a silicon wafer, such as a four inch silicon wafer. Firstly the wafer is baked at 120° C. to remove moisture from the wafer. This baking can occur for thirty minutes.

A layer 202 of silicon dioxide is deposited, preferably to a thickness of about 1 μm. Silicon dioxide can be deposited by thermal deposition or by CVD (chemical vapour deposition). The wafer 200 and layer 202 form the base layer, to which the body region 110 of the device 100 is coupled. Ultimately, flexible elements 102, 104 and 106 will flex towards and away from the layer 202.

Subsequently, a layer 204 of chromium is deposited on the surface, followed by a thicker layer of gold 206. Both the chromium and gold can be deposited by plasma sputtering. Typically, the layer 204 of chromium will be 50 nm thick and the layer of gold approximately 150 nm thick. The chromium layer is used as a seed layer, for the subsequent formation of the gold structural layer 206.

FIG. 5B illustrates the substrate after it has been patterned via use of a first optical mask. Firstly, a further dehydration bake is performed e.g. at 120° C. for approximately 30 minutes. A layer of suitable resist is then coated on top of the gold and chromium. The resist is suitable for masking during the etching of both gold and chromium. Suitable resists include JSR's chemically amplified positive tone phptoresist or AZ5214E positive tone I-line photoresist from AZ Electronic Materials, or equivalent.

Subsequently, the resist layer is exposed via the optical mask, so as to transfer the pattern from the first optical mask on to the resist layer. The patterned openings are of rectangular shape and will provide the freeing region from which the flexible members 102, 104, 106 and coupling member 120 are subsequently released from being coupled to the substrate.

The exposed resist coating is then developed, and the relevant portions of the layers 206, 204 etched away. The remaining resist is then stripped away. This can be facilitated by oxygen plasma descuming of the resist material/adhesive of the resist. The structure remaining is that indicated in FIG. 5B. The portions of the gold and chromium on the left hand side of the Figure provide the base of the subsequent body region 110. The gaps in the gold and chromium layers 204, 206, defined by the etching process, are the regions in which the flexible elements 102, 104, 106 and coupling member 120 are subsequently formed.

FIG. 5C shows the results of the deposition of the first structural layer. Typically, the surface will be prepared by again dehydration baking of the structure at 120° C. for 30 minutes. A further layer of gold 207 is then deposited, followed by another layer of chromium 208 and a third layer of gold 210. Typically, the additional gold layer 207 will be approximately 100 nm thick, the chromium layer 208 50 nm thick and the final gold layer 210 relatively thick compared to the layers e.g. approximately 750 nm thick (i.e. a thickness of about 1 μm). The gold layer 210 forms one layer of the laminate structure of the flexible elements (i.e. laminate layer 108b). In the final structure realised by this application sequence (see FIG. 5Q), it can be seen that the chromium layer also extends to the end of the flexible elements, and forms an outer layer within the flexible elements. This layer is acting as the etch-stop layer to control the wet etching processing of gold layer during the patterning of flexible members (FIG. 5P).

FIG. 5D shows the results of patterning the first structural layer, using a second optical mask. Again, the dehydration bake at 120° C. is performed for about 30 minutes. A suitable resist coating (again, JSR or AZ5214E, or equivalent) is then utilised, and placed over the outermost surface of the gold layer 210, illustrated in FIG. 5C.

The resist is then exposed via the second optical mask, so as to define the region where the coupling member 120 is going to be formed and to etch the metal excess in order to reduce the thermal conductivity across the paddle. The partially exposed resist coating is then developed, and subsequently etches performed upon the outer gold layer 210 and the adjacent chromium layer 208, to remove portions of those layers (as defined by the second optical mask). The resist is again stripped away, and preferably descuming performed via oxygen plasma. The resulting structure is shown in FIG. 5D. The gap 302 in layers 208, 209 formed by the patterning process ultimately defines the free ends of the flexible elements (i.e. the ends of the flexible elements distant from the body region 110 in the final device, which are connected to coupling member 120).

FIG. 5E shows the results of the deposition of the second structural layer i.e. the first portion of the laminate layer 108a. In this particular embodiment, the laminate layer 108a is formed of polyimide. To obtain this structure, firstly a dehydration bake at 120° C. is performed for 30 minutes. A coating of polyimide with typical thickness between 2 μm-4 μm (e.g. PI2562 or PI2566 from DuPont's Pyralin Polyimide Family PI2560 or equivalent) is provided. To enable the coating 212a to set, the coating is then baked e.g. in a programmable oven.

Preferably, the baking occurs via slowly ramping up the temperature of the oven containing the structure from room temperature to the baking temperature. An appropriate ramping rate might be several degrees Celsius per minute. The structure is then held at the baking temperature, and then the temperature of the oven slowly increased to a final, upper temperature (e.g. at a rate of several degrees Celsius per minute), with the structure then being held at the final temperature for about an hour. For example, the oven could be ramped at 3° C. per minute from room temperature to 200° C., held at 2000 C for thirty minutes, and then a temperature increased to a temperature not exceeding 3500 C at a slow ramp rate of approximately 2° C. per minute, with the temperature being then held at that final temperature for sixty minutes. The structure is then allowed to cool naturally (i.e. without enforced cooling) to room temperature. That completes the processing of the first portion of the polyimide layer 212 (the first portion being layer 212a). Different polyimide layers 212b, 212c are deposited in subsequent steps, so as to enclose the relevant movement sensors/actuators (e.g. heater elements) that are subsequently formed.

FIG. 5F shows the results of a first registration step, using a third optical mask. The registration step is performed so as to provide indentations for registration marks for subsequent alignment of optical masks 4-7.

Firstly, dehydration baking is performed, then the upper surface coated with the resist coating (again, JSR or AZ5214E or similar), the exposure step performed using the third mask, and then the exposed resist developed. A dry etch (e.g. via oxygen plasma) is then performed (e.g. for four minutes) to remove a portion of the polyimide structure (as defined by the third optical mask) to leave the desired indentations in the polyimide structure 212a. The remaining resist material can then be stripped away.

FIG. 5G shows the results of the first metallisation step. Again, a dehydration bake is first performed at 120° C. for about thirty minutes. A thin-film layer of metal typically between 50 nm and 250 nm is then deposited e.g. by plasma sputtering. The thin layer material is that utilised to form either the actuation tracks, or the sensor tracks. In this particular embodiment, this layer is used to form the actuation tracks, and hence a suitable material (such as chromium/gold alloy, aluminium, or nichrome) is utilised. Such a material can be deposited via plasma sputtering. FIG. 5G shows the results of a layer 214 of that material after it is deposited by plasma sputtering, with the layer 214 extending/being secured to the polyimide layer 212a via the indentations formed in the registration step (see FIG. 5F). The resulting structure is shown in FIG. 5G.

FIG. 5H shows the results of the subsequent patterning of the relevant tracks using a fourth optical mask i.e. the subsequent patterning of the actuation tracks. The fourth optical mask utilised here defines the shape of the actuation tracks. Again, the material is first dehydration baked at 120° C. for twenty minutes. A layer of suitable resist coating is then applied (e.g. JSR or AZ5214E or equivalent) and the material exposed via the optical mask to transfer the pattern of the actuation tracks on to the resist. The resist is then developed, and metal etching performed so as to define the actuation track pattern within the layer 214. Thus, the actuation tracks 112 are formed. The metal etching is typically wet metal etching. The remaining resist layer is then stripped away.

FIG. 5I shows the results of the deposition of the third structural layer. In particular, an additional layer of the laminate material (i.e. a second layer of polyimide) is deposited. This second layer 212b of polyimide is provided so as to encapsulate the actuation tracks 214/112. The layer 212b is approximately 2 μm-4 μm thick. These steps required to deposit this layer 212b of polyimide are the same as those used to deposit the layer of polyimide described with respect to FIG. 5E.

FIG. 5I shows the results of a second metallisation step, which is used to deposit the material for the other set of tracks (in this particular instance, the material that ultimately forms the sensor tracks 116). Again, the structure is first dehydration baked. The metal layer 216 is then deposited. This layer is deposited as a thin-film of typical thickness between 50 nm and 250 nm. The deposition can be performed by plasma sputtering. Suitable materials include chromium/gold or platinum, or preferably, in this particular embodiment, nichrome or chromium-copper alloy are utilised to form the metal layer 216 shown in FIG. 5J because of their low temperature coefficients.

FIG. 5K shows the results of the patterning of the movement sensor tracks, using a fifth optical mask to define the shape of the track from the layer material deposited in the previous step. This track patterning is performed using the same steps described for the patterning of the actuation tracks, with reference to FIG. 5H.

Subsequently, another layer 212c of polyimide is provided, so as to encapsulate the patterned signal tracks 216. This layer of polyimide is deposited using the same steps described with reference to FIG. 5I, for depositing the second layer 212b of polyimide. Alternative materials for encapsulation include thin (50 nm) $Si_3N_4$, $SiO_2$ or similar, deposited by plasma deposition. The encapsulated structure is illustrated in FIG. 5L.

Subsequently, the flexible members are patterned and the openings formed for subsequently providing contact pads for the sensing and actuation tracks (i.e. the openings are formed for pads 114, 118 shown in FIG. 2). This patterning of the flexible elements and providing the openings for the pads can be performed in a single step, using a further (sixth) optical mask. The result is illustrated in FIG. 5M.

Firstly, the structure is dehydration baked. A layer of relatively thick resist coating (8 μm-12 μm) is then applied (e.g. AZ4562 or AZ9260 positive thone photoresists from AZ Electronic Materials, or equivalent).

The structure is then soft baked, the resist coating exposed via the sixth optical mask, and then the resist coating developed. Thus, the mask will define the structure of both the openings for the pads, and the end of the cantilever. An etch is then performed so as to remove the relevant portions of polyimide defined by the mask. This can be a dry etch, for instance performed using a mixture of oxygen and tetrafluoromethane. As per the previous steps, the remainder of the resist layer is subsequently stripped, and the surface descumed. This leaves the structure illustrated in FIG. 5M. As can be seen, the structure includes opening 304, 306 through the polyimide layer to the tracks 214, 216. These openings 304, 306 are subsequently used for providing the electrical contact pads. Further, an opening 308 is provided to layer 210. One surface 310 defining this opening 308 forms the end surface of the coupling member 120 in the final device.

Subsequently, as illustrated in FIG. 5N, the material 218 forming the electrical contact pads is deposited. Firstly, the structure is dehydration baked. The material forming the contact pads is then deposited. Typically, the material will be a metal (aluminium or chromium/gold). The material is deposited as a thick metal layer (e.g. approximately 1 μm thick). The metal layer can be deposited by plasma sputtering. A thick resist coating (AZ4562 or AZ9260) is then applied, and a soft bake performed on the thick resist coating. The coating is then exposed via a seventh optical mask, so as to define the structure of the contact pads 218 (i.e. to remove the excess additional material deposited by the plasma sputtering step). Subsequently, the resist coating is developed, and the superfluous metal removed e.g. by wet etching. Again, the remaining resist is then stripped, and the outer surface descumed, to leave the structure shown in FIG. 5N.

Finally, the patterned devices are prepared for extraction from the wafer in the form of rectangular chips, followed by the releasing of cantilevers to form the free standing structures. A thick resist coating (8 μm-12 μm of AZ4562 or AZ9260) is applied, and then a soft bake performed (FIG. 5O). The coating is then exposed via third optical mask (used also for registration, with rectangular openings matching the ones of the optical mask 1 and with superimposed cantilever and paddle footprints).

Prior to photoresist development the wafer is scored (e.g. indentation cuts across the whole wafer in X and Y directions by a diamond dicing saw with 100 μm wide blade) with appropriate steps in order to define the device chip area in the silicon substrate. (FIG. 5P) The wafer is not cut through in order to carry out the final preparation for releasing of cantilevers on a wafers scale. Alternatively, the scoring of the wafers can be performed in the initial stages of the fabrication process and prior to any patterning.

Following the wafers scoring, the photoresist is developed and exposed gold/chromium layer etched, wafer rinsed and dried. At this stage individual chips are extracted from the wafer (by snapping along the scored lines). A final gold etch is performed (FIG. 5Q). The bottom chromium layer (50 nm thick) in the cantilevers region, that was acting as an etch stop during the final cantilever patterning and release, can optionally be stripped in a wet etch bath.

FIG. 5Q shows the results of the final device preparation and packaging. The remaining resist is stripped away, and the structure rinsed and dried. Preferably, the structure is then mounted on a suitable carrier, such as a CerDIP carrier (Ceramic Dual-in-line headers with 8, 12, 16, 24 or more leads/pins). Wires can then be bonded to the electrical contact pads for the operation of the device. The resulting structure formed can be that shown in FIGS. 1A, 1B and 2.

The invention claimed is:

1. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element; and
wherein said first flexible element is coupled to said second flexible element at a position distant from said body region, and the actuating portion of said first flexible element is operable to move the first and second flexible elements;
wherein each of said first and second flexible elements moves from said first respective configuration to said second respective configuration via bending of the first flexible element in a respective bending plane, and the first and second flexible elements are coupled together via a coupling member extending between the first and second flexible elements in a direction substantially perpendicular to the bending plane.

2. A device as claimed in claim 1, wherein said coupling member is formed of a substantially rigid material.

3. A device as claimed in claim 1, wherein the coupling member is shaped to act as a paddle as the first and second flexible elements move between said first and second respective configurations.

4. A device as claimed in claim 1, wherein said coupling member is connected to the second ends of the first and second flexible elements.

5. A device as claimed in claim 4, wherein said coupling member extends in a plane away from the first and second flexible elements.

6. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective, configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
at least two of said first flexible elements, the second flexible element being located between the two first flexible elements.

7. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;

said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
wherein said first flexible element is coupled to said second flexible element via a thermally insulative material.

8. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
wherein said first flexible element is coupled to said second flexible element at a plurality of positions.

9. A device as claimed in claim 8, wherein the length of the first and second flexible elements from the first end to the second end is within the range from about 100 to about 1000 μm.

10. A device as claimed in claim 8, wherein the distance between the second end of the second flexible element in said first respective configuration and the second end of the second flexible element in said second respective configuration lies within the range from about 20 to about 650 μm.

11. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
wherein said first and second flexible elements extend longitudinally, with the first flexible element being coupled to said second flexible element along the complete length of said first and second flexible elements.

12. A device as claimed in claim 11, wherein the length of the first and second flexible elements from the first end to the second end is within the range from about 100 to about 1000 μm.

13. A device as claimed in claim 11, wherein the distance between the second end of the second flexible element in said first respective configuration and the second end of the second flexible element in said second respective configuration lies within the range from about 20 to about 650 μm.

14. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
wherein the actuating portion of said first flexible element comprises:
a laminate of at least two layers, having different coefficients of thermal expansion; and
a heater element for heating the flexible element to induce bending of the element.

15. A device as claimed in claim 14, wherein a first layer of the laminate comprises a polymer, and a second layer of the laminate comprises a metal.

16. A device as claimed in claim 14, wherein a first layer of the laminate comprises a polymer, and a second layer of the laminate comprises a polymer.

17. A device as claimed in claim 14, wherein said layers have a Young's modulus of less than 1000 Pa, and a coefficient of thermal expansion at room temperature of greater than 10E-06 deg. Kelvin.

18. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and wherein said movement sensor is arranged such that an electrical property of the movement sensor changes due to movement of said second flexible element.

19. A device as claimed in claim 18, wherein said movement sensor comprises a piezoresistive element arranged such that the electrical resistance of the piezoresistive element changes as the second flexible element bends.

20. A device as claimed in claim 19, wherein said piezoresistive element comprises at least one of nichrome, chromium, copper, or chrome copper alloy.

21. A device as claimed in claim 19, wherein said piezoresistive element comprises at least one of aluminum nitride, lead zirconate titanate, polycrystalline silicon, or electrically conductive polymers.

22. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
wherein the length of the first and second flexible elements from the first end to the second end is within the range from about 100 to about 1000 μm.

23. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
wherein the distance between the second end of the second flexible element in said first respective configuration and the second end of the second flexible element in said second respective configuration lies within the range from about 20 to about 650 μm.

24. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
an electronic circuit coupled to the first flexible element and arranged to provide a signal to the actuator portion for moving the first flexible element from the first respective configuration to the second respective configuration, and coupled to the movement sensor of the second flexible element, and arranged to provide an output signal indicative of the movement sensed by said movement sensor.

25. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
said first flexible element comprising an actuating portion arranged to move the first flexible element between the first respective configuration and the second respective configuration;
said second flexible element comprising an integral movement sensor for sensing movement of the second flexible element;
wherein said first flexible element is coupled to said second flexible element at a position distant from said body region, and the actuating portion of said first flexible element is operable to move the first and second flexible elements; and
wherein the actuating portion of said second flexible element is not operable to move the first and second flexible elements.

26. A device for detecting a property of a fluid, comprising:
a body region;
a first flexible element and a second flexible element, each of the first and second flexible elements having a first end and a second end, said first end being fixedly located on said body region, and each of the first and second flexible elements being moveable from at least a first respective configuration to a second respective configuration via bending of the respective flexible element;
wherein said first flexible element is coupled to said second flexible element at a position distant from said body region;
said first flexible element comprising an actuating portion arranged to move the first and second flexible elements between the first respective configuration and the second respective configuration;
said second flexible element comprising an integral movement sensor for sensing movement of the second flexible element;

wherein the actuating portion of said first flexible element is operable to move the first and second flexible elements;
wherein the actuating portion of said first flexible element comprises:
a laminate of at least two layers, having different coefficients of thermal expansion;
a heater element for heating the first flexible element to induce bending of the first flexible element;
wherein said movement sensor is arranged such that an electrical property of the movement sensor changes due to movement of said second flexible element; and
wherein said movement sensor comprises a piezoelectric element arranged such that the electrical signal of the piezoelectric element changes as the second flexible element bends.

27. A device as claimed in claim 26, wherein each of said first and second flexible elements extends longitudinally, substantially parallel to each other.

28. A device as claimed in claim 26, wherein the length of the first and second flexible elements from the first end to the second end is within the range from about 100 to about 1000 μm.

29. A device as claimed in claim 26, wherein the distance between the second end of the second flexible element in said first respective configuration and the second end of the second flexible element in said second respective configuration lies within the range from about 20 to about 650 μm.

* * * * *

UNITED STATES PATENT AND TRADEMARK OFFICE
CERTIFICATE OF CORRECTION

PATENT NO. : 8,297,110 B2
APPLICATION NO. : 12/293234
DATED : October 30, 2012
INVENTOR(S) : Vladislav Djakov et al.

It is certified that error appears in the above-identified patent and that said Letters Patent is hereby corrected as shown below:

In column 14, line 17, delete "FIG. 5I" and insert in lieu thereof -- FIG. 5J --.

Signed and Sealed this
Nineteenth Day of March, 2013

Teresa Stanek Rea
*Acting Director of the United States Patent and Trademark Office*